United States Patent
Shanahan et al.

(10) Patent No.: US 10,512,269 B2
(45) Date of Patent: Dec. 24, 2019

(54) HERBICIDAL COMPOUNDS

(71) Applicant: Syngenta Participations AG, Basel (CH)

(72) Inventors: Stephen Edward Shanahan, Bracknell (GB); Timothy Jeremiah Cornelius O'Riordan, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 15/569,885

(22) PCT Filed: Apr. 27, 2016

(86) PCT No.: PCT/EP2016/059383
§ 371 (c)(1),
(2) Date: Oct. 27, 2017

(87) PCT Pub. No.: WO2016/174075
PCT Pub. Date: Nov. 3, 2016

(65) Prior Publication Data
US 2018/0110227 A1  Apr. 26, 2018

(30) Foreign Application Priority Data

Apr. 30, 2015 (GB) .................................. 1507463.6

(51) Int. Cl.
| A01N 43/90 | (2006.01) |
| A01N 43/78 | (2006.01) |
| C07D 513/04 | (2006.01) |
| C07D 417/12 | (2006.01) |
| C07D 277/60 | (2006.01) |

(52) U.S. Cl.
CPC ............. *A01N 43/90* (2013.01); *A01N 43/78* (2013.01); *C07D 277/60* (2013.01); *C07D 417/12* (2013.01); *C07D 513/04* (2013.01)

(58) Field of Classification Search
None
See application file for complete search history.

(56) References Cited

U.S. PATENT DOCUMENTS

2012/0058893 A1    3/2012  Lehr et al.
2017/0347654 A1*  12/2017  Shanahan ............ C07D 513/04

FOREIGN PATENT DOCUMENTS

| GB | 2525270 A    | 10/2015 |
| WO | 2011/051212 A1 | 5/2011 |
| WO | 2011/117195 A1 | 9/2011 |
| WO | 2012/028582 A1 | 3/2012 |
| WO | 2013/144096 A1 | 10/2013 |

OTHER PUBLICATIONS

International Search Report for International Patent Application No. PCT/EP2016/059378 dated Jun. 1, 2016.
GB Search Report for GB Patent Application No. GB1507463.6 dated Jan. 22, 2016.

* cited by examiner

*Primary Examiner* — Alton N Pryor
(74) *Attorney, Agent, or Firm* — BakerHostetler LLP; Toni-Junell Herbert

(57) ABSTRACT

The present invention relates to herbicidal heteroaryl-alkyl-oxy-substituted heteroaryl/phenyl derivatives of formula (I), as well as to processes and intermediates used for the preparation of such derivatives. The invention further extends to herbicidal compositions comprising such derivatives, as well as to the use of such compounds and compositions in controlling undesirable plant growth; in particular the use in controlling weeds in crops of useful plants.

15 Claims, No Drawings

HERBICIDAL COMPOUNDS

RELATED APPLICATION INFORMATION

This application is a 371 of International Application No. PCT/EP2016/059383, filed Apr. 27, 2016, which claims priority to GB Application No. 1507463.6 filed Apr. 30, 2015, the contents of which are incorporated herein by reference herein.

The present invention relates to herbicidal heteroaryl-alkyl-oxy-substituted heteroaryl/phenyl derivatives of formula (I), as well as to processes and intermediates used for the preparation of such derivatives. The invention further extends to herbicidal compositions comprising such derivatives, as well as to the use of such compounds and compositions in controlling undesirable plant growth; in particular the use in controlling weeds, such as broad-leaved dicotyledonous weeds, in crops of useful plants.

The prior art describes various herbicidally active pyridinones forming a condensed ring system with either five- or six-membered heterocyclic rings. For example WO2011/051212 discloses pyridinones which are condensed with selected five-membered heterocycles and which are substituted in the 3 position of the pyridine ring by aryl and heteroaryl radicals. WO2012/028582 discloses pyridinones which are condensed with selected five- and six-membered heterocycles and which are substituted in the 3 position of the pyridine ring by aryl radicals. WO2013/144096 describes herbicidally and insecticidally active thiazolopyridinones, which are substituted in the 3 position of the pyridine ring by aryl or heteroaryl radicals.

The present invention is based on the finding that heteroaryl-alkyl-oxy-substituted heteroaryl/phenyl derivatives of formula (I) exhibit surprisingly good herbicidal activity.

Thus, in a first aspect there is provided a compound of formula (I),

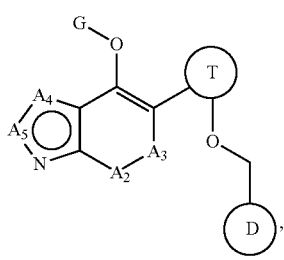

or a salt or N-oxide thereof, wherein, $A_2$ is $CR^{10a}R^{10b}$ or $NR^{11}$;
$A_3$ is $C(O)$ or $S(O)_2$;
$A_4$ is $CR^1$, $N(R^{13})_n$, O or S;
$A_5$ is $CR^2$, $N(R^{14})_n$, O or S;
n is an integer of 0 or 1;
$R^1$ is independently hydrogen, halogen, nitro, cyano, or independently selected from the group consisting of: $C_1$-$C_6$alkyl, $C_2$-$C_6$ alkenyl, $C_1$-$C_6$ alkoxy $C_1$-$C_6$ alkylthio, $C_1$-$C_6$alkylsulfinyl, $C_1$-$C_6$alkylsulfonyl, $C_3$-$C_6$cycloalkyl, $C_1$-$C_6$ alkoxy-$C_1$-$C_6$alkyl-, $C_1$-$C_6$alkoxy-$C_1$-$C_6$alkoxy-, di-$C_1$-$C_6$alkoxy-$C_1$-$C_6$alkyl, and $C_1$-$C_6$alkylthio-$C_1$-$C_6$alkyl, each of which is optionally substituted by 1-3 halogen atoms;
$R^2$ is hydrogen, halogen, methyl or $C_1$haloalkyl;
$R^{10a}$ and $R^{10b}$ are each independently hydrogen, halogen, cyano, $C_1$-$C_8$alkyl, $C_1$-$C_8$alkoxy-$C_1$-$C_4$alkyl-, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkyl-, heterocyclyl, heterocyclyl-$C_1$-$C_4$alkyl-, or $C_1$-$C_8$alkoxycarbonyl-; or $R^{10a}$ and $R^{10b}$ together with the carbon atom they are attached to join to form a 3- to 10-membered carbocyclic ring or a 4- to 10-membered heterocyclic ring;
$R^{11}$ is hydrogen, $C_1$-$C_{10}$alkyl, $C_1$-$C_4$haloalkyl, $C_2$-$C_{10}$alkenyl, $C_2$-$C_4$haloalkenyl, $C_2$-$C_{10}$alkynyl, $C_2$-$C_4$haloalkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^{12}$, or heterocyclyl-$C_1$-$C_6$alkyl- or heterocyclyl-$C_1$-$C_6$alkyl- wherein the heterocyclyl moiety is substituted by one to three $R^{12}$;
each $R^{12}$ is independently halogen, $C_1$-$C_4$alkyl, $C_1$-$C_4$haloalkyl, $C_1$-$C_4$alkoxy or $C_1$-$C_4$haloalkoxy;
$R^{13}$ is hydrogen, $C_1$-$C_3$alkyl, or $C_1$-$C_3$haloalkyl;
$R^{14}$ is hydrogen, methyl or $C_1$haloalkyl;
G is hydrogen, or $C(O)R^3$;
$R^3$ is selected from the group consisting of $C_1$-$C_6$alkyl, $C_1$-$C_6$alkenyl, $C_1$-$C_6$alkynyl, $C_1$-$C_6$alkoxy, $C_1$-$C_6$alkyl-S—, —$NR^4R^5$ and phenyl optionally substituted by one or more $R^6$;
$R^4$ and $R^5$ are independently selected from the group consisting of $C_1$-$C_6$ alkyl and $C_1$-$C_6$ alkoxy, or $R^4$ and $R^5$ together can form a morpholinyl ring;
$R^6$ is selected from the group consisting of halogen, cyano, nitro, $C_1$-$C_3$alkyl, $C_1$-$C_3$haloalkyl, $C_1$-$C_3$alkoxy and $C_1$-$C_3$haloalkoxy; and
T is a 5- or 6-membered monocyclic heteroaryl ring system containing 1, 2, or 3 heteroatoms independently selected from nitrogen, oxygen and sulphur, said 5-membered ring system being substituted by one or more radicals selected from X, Y, and $R^7$, and said 6-membered ring system being substituted by one or more radicals selected from $X^1$, $X^2$, $X^3$, $X^4$ and $R^7$, and wherein the oxy-alkyl-D moiety and the bi-cyclic moiety are linked via ring T such that they are situated ortho with respect to each other;

or T is a substituted phenyl ring of formula (Tp)

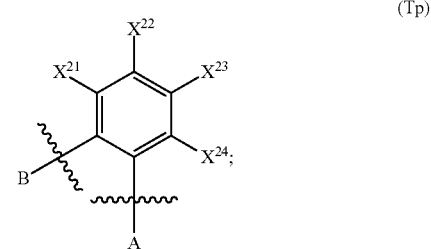

each X, $X^3$, $X^{23}$ and each Y are independently hydrogen, $C_1$-$C_3$ alkyl, $C_1$-$C_3$ alkoxy, $C_1$-$C_3$haloalkyl, $C_1$-$C_3$haloalkoxy, or halogen;

$X^1$ is oxo, $C_1$-$C_3$ alkyl, $C_1$-$C_3$ alkoxy, $C_1$-$C_3$haloalkyl, $C_1$-$C_3$haloalkoxy, or halogen;

$X^2$, and $X^4$ are independently hydrogen, $C_1$-$C_3$ alkyl, $C_1$-$C_3$ alkoxy, $C_1$-$C_3$haloalkyl, $C_1$-$C_3$haloalkoxy, oxo, or halogen;

$X^{21}$ is $C_1$-$C_3$ alkyl, $C_1$-$C_3$ alkoxy, $C_1$-$C_3$haloalkyl, $C_1$-$C_3$haloalkoxy, or halogen;

$X^{22}$, and $X^{24}$ are independently hydrogen, $C_1$-$C_3$ alkyl, $C_1$-$C_3$ alkoxy, $C_1$-$C_3$haloalkyl, $C_1$-$C_3$haloalkoxy, or halogen;

$R^7$ is hydrogen, $C_1$-$C_3$ alkyl, $C_1$-$C_3$ alkoxy, $C_1$-$C_3$haloalkyl, $C_1$-$C_3$haloalkoxy;

A denotes the point of attachment to the oxy-alkyl-D moiety and B denotes the point of attachment to the bicyclic moiety and D is a substituted or unsubstituted monocyclic heteroaryl ring containing 1, 2, or 3 heteroatoms independently selected from oxygen, nitrogen and sulphur, and wherein when D is substituted it is substituted on at least one ring carbon atom with $R^8$ and/or on a ring nitrogen atom with $R^9$; or D is the group (Dp)

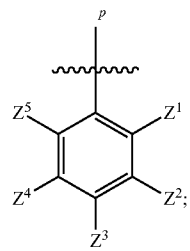

(Dp)

each $R^8$ is independently oxygen, hydroxyl, halogen, cyano, $C_1$-$C_6$alkyl, $C_1$-$C_6$haloalkyl, $C_1$-$C_6$haloalkoxy, $C_1$-$C_3$haloalkoxy-$C_1$-$C_3$alkyl-, $C_1$-$C_6$alkoxy, $C_1$-$C_3$alkoxy-$C_1$-$C_3$alkyl, $C_1$-$C_3$alkoxy-$C_1$-$C_3$alkoxy-$C_1$-$C_3$alkyl-, $C_3$-$C_6$cycloalkyl, $C_2$-$C_6$ alkenyl, $C_2$-$C_6$ haloalkenyl, $C_2$-$C_6$ alkynyl, $C_1$-$C_6$hydroxyalkyl-, $C_1$-$C_6$alkylcarbonyl-, $C_1$-$C_6$alkyl-S(O)$_m$—, amino, $C_1$-$C_6$alkylamino, $C_1$-$C_6$dialkylamino, —C($C_1$-$C_3$alkyl)=N—O—$C_1$-$C_3$alkyl and $C_2$-$C_6$ haloalkynyl;

m is an integer of 0, 1, or 2; and each $R^9$ is independently, $C_1$-$C_4$ alkyl, $C_3$-$C_6$alkoxy, $C_1$-$C_2$ alkoxy-$C_1$-$C_2$ alkyl, $C_2$-$C_4$ alkenyl, $C_1$-$C_4$ haloalkyl, $C_2$-$C_4$ haloalkenyl, $C_2$-$C_4$ alkynyl or $C_2$-$C_4$ haloalkynyl;

p denotes the point of attachment of (Dp) to the rest of the molecule; and $Z^1$, $Z^2$, $Z^3$, $Z^4$, and $Z^5$ are each independently selected from hydrogen, $C_1$-$C_3$ alkyl, $C_1$-$C_3$ alkoxy, $C_1$-$C_3$haloalkyl, $C_1$-$C_3$haloalkoxy, or halogen;

provided that when $A_4$ is S, $A_2$ is $NR^{11}$, and $A^3$ is C(O), then T is not (Tp) when D is (Dp).

Compounds of Formula (I) may contain asymmetric centres or an axis of chirality and may be present as a single enantiomer, pairs of enantiomers in any proportion or, where more than one asymmetric centre/axis of chirality is present, contain diastereoisomers in all possible ratios. Typically one of the enantiomers has enhanced biological activity compared to the other possibilities.

Similarly, where there are di-substituted alkenes, these may be present in E or Z form or as mixtures of both in any proportion.

Furthermore, compounds of formula (I) may be in equilibrium with alternative tautomeric forms. For example, a compound of formula (I-i), i.e. a compound of formula (I) wherein $A_2$ is $NR^{11}$, $R^{11}$ is hydrogen, $A_3$ is C(O), and G is hydrogen, can be drawn in at least five tautomeric forms:

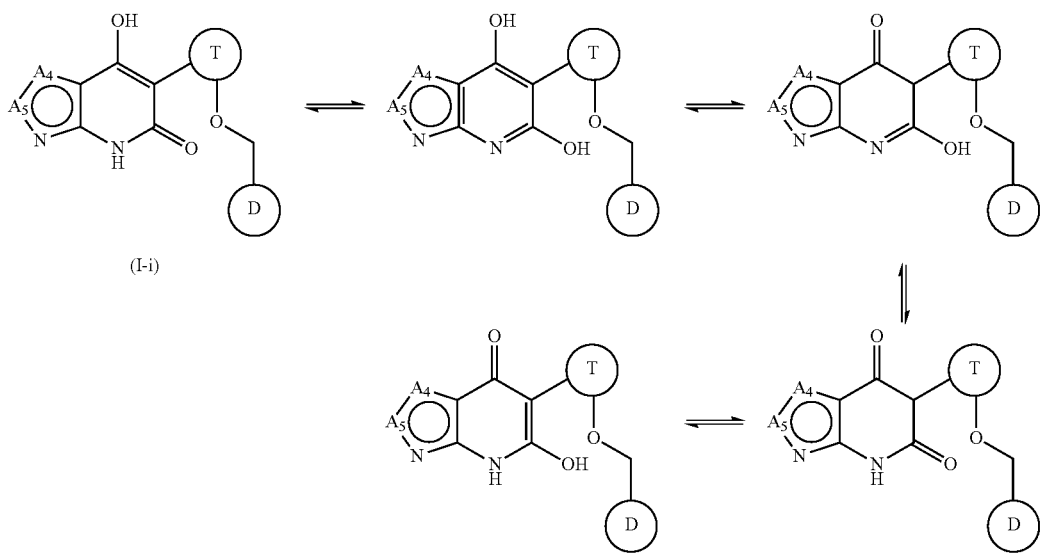

(I-i)

Similarly, a compound of formula (I-ii), i.e. a compound of formula (I) wherein $A_2$ is $CR^{10a}R^{10b}$, $A_3$ is S(O)$_2$, and G is hydrogen, can be drawn in two tautomeric forms:

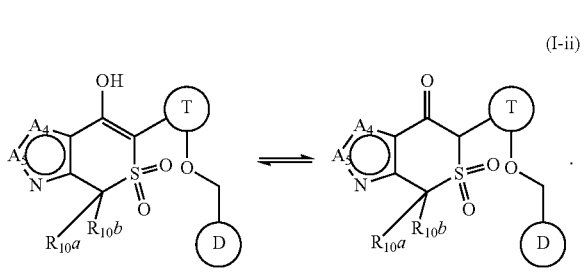

It should be appreciated that all tautomeric forms (single tautomer or mixtures thereof), racemic mixtures and single isomers are included within the scope of the present invention.

Each alkyl moiety either alone or as part of a larger group (such as alkoxy, alkylthio, alkoxycarbonyl, alkylcarbonyl, alkylaminocarbonyl, or dialkylaminocarbonyl, et al.) may be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups are generally $C_1$-$C_6$alkyl groups (except where already defined more narrowly), but are preferably $C_1$-$C_4$alkyl or $C_1$-$C_3$alkyl groups, and, more preferably, are $C_1$-$C_2$alkyl groups (such as methyl).

Alkenyl and alkynyl moieties can be in the form of straight or branched chains, and the alkenyl moieties, where appropriate, can be of either the (E)- or (Z)-configuration. The alkenyl or alkynyl moieties are typically $C_2$-$C_4$alkenyl or $C_2$-$C_4$alkynyl, more specifically vinyl, allyl, ethynyl, propargyl or prop-1-ynyl. Alkenyl and alkynyl moieties can contain one or more double and/or triple bonds in any combination; but preferably contain only one double bond (for alkenyl) or only one triple bond (for alkynyl).

Preferably, the term cycloalkyl refers to cyclopropyl, cyclobutyl, cyclopentyl or cyclohexyl.

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents may be present on the same carbon atom.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-S(O)$_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

The term "heterocyclyl" as used herein, encompasses ring systems containing at least one heteroatom and that are typically in monocyclic form. Preferably, heterocyclyl groups will contain up to two heteroatoms which will preferably be chosen from nitrogen, oxygen and sulfur. Such heterocyclyl groups are preferably 3- to 8-membered, and more preferably 3- to 6-membered rings. Examples of heterocyclic groups include oxetanyl, thietanyl, and azetidinyl groups. Heterocyclyl groups containing a single oxygen atom as heteroatom are preferred.

The term "heteroaryl" as used herein means an aromatic ring system containing at least one ring heteroatom and consists of a single ring. Preferably, single rings will be 5-or-6-membered and contain 1, 2 or 3 ring heteroatoms selected independently from nitrogen, oxygen and sulfur. Typically "heteroaryl" is as used in the context of this invention includes furyl, thienyl, pyrrolyl, pyrazolyl, imidazolyl, triazolyl, oxazolyl, isoxazolyl, thiazolyl, isothiazolyl, oxadiazolyl, pyridyl, pyrimidinyl, pyridazinyl, pyrazinyl, and triazinyl rings, which may or may not be substituted as described herein.

The group (B)

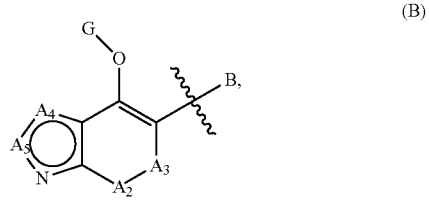

(B)

wherein $A_2$, $A_3$, $A_4$, $A_5$, and G are as defined herein,
is referred to herein as the bicyclic moiety, wherein B denotes the point of attachment to the rest of the molecule (i.e. to the optionally substituted heteroaryl-alkyl-oxy-heteroaryl/phenyl moiety, which may also be referred to as the -T-O—CH$_2$-D moiety).

The present invention also includes agronomically acceptable salts that the compounds of formula (I) may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used. The compounds of formula (I) according to the invention also include hydrates which may be formed during the salt formation.

Preferred values of $A_2$, $A_3$, $A_4$, $A_5$, $R^1$, $R^2$, $R^3$, $R^4$, $R^5$, $R^6$, $R^7$, $R^8$, $R^9$, $R^{10a}$, $R^{10b}$, B, G, D, X, $X^1$, $X^2$, $X^3$, $X^4$, $X^{21}$, $X^{22}$, $X^{23}$, $X^{24}$, Y, $Z^1$, $Z^2$, $Z^3$, $Z^4$, $Z^5$, and m are as set out below, and a compound of formula (I) according to the invention may comprise any combination of said values. The skilled man will appreciate that values for any specified set of embodiments may be combined with values for any other set of embodiments where such combinations are not mutually exclusive.

As stated herein, $A_2$ is $CR^{10a}R^{10b}$ or $NR^{11}$. Where $A_2$ is $CR^{10a}CR^{10b}$, preferably $R^{10a}$ and $R^{10b}$ are each independently hydrogen, halogen, $C_1$-$C_8$alkyl, $C_1$-$C_8$haloalkyl or $C_2$-$C_8$alkynyl. Examples of preferred groups for $R^{10a}$ and $R^{10b}$ include fluoro, methyl, ethyl, difluoroethyl and propargyl. In one preferred embodiment $R^{10a}$ and $R^{10b}$ are each methyl. In a further embodiment where $R^{10a}$ and $R^{10b}$ together with the carbon atom they are attached to join to form a carbocyclic ring, the carbocyclic ring is preferably cyclopropyl.

Where $A_2$ is $NR^{11}$, $R^{11}$ is preferably hydrogen, $C_1$-$C_6$alkyl, $C_1$-$C_3$haloalkyl, $C_2$-$C_6$alkenyl, $C_2$-$C_4$haloalkenyl, $C_2$-$C_4$alkynyl, $C_2$-$C_4$haloalkynyl, $C_3$-$C_6$cycloalkyl, $C_3$-$C_6$cycloalkyl-$C_1$-$C_4$alkyl-, $C_1$-$C_6$alkoxy-$C_1$-$C_4$alkyl-, $C_1$-$C_6$cyanoalkyl-, $C_1$-$C_6$alkoxycarbonyl-$C_1$-$C_4$alkyl-, N—$C_1$-$C_3$alkyl-aminocarbonyl-$C_1$-$C_3$alkyl-, N,N-di-($C_1$-$C_3$alkyl)-aminocarbonyl-$C_1$-$C_4$alkyl-, aryl-$C_1$-$C_4$alkyl- or aryl-$C_1$-$C_4$alkyl- wherein the aryl moiety is substituted by one to three $R^{12}$, or heterocyclyl-$C_1$-$C_4$alkyl- or heterocyclyl-$C_1$-$C_4$alkyl- wherein the heterocyclyl moiety is substituted by one to three $R^{12}$, wherein $R^{12}$ is preferably chloro, bromo, fluoro, $C_1$-$C_3$alkyl, $C_1$-$C_3$haloalkyl, $C_1$-$C_3$alkoxy or $C_1$-$C_3$haloalkoxy.

More preferably $R^{11}$ is hydrogen, $C_1$-$C_4$alkyl, $C_1$-$C_4$haloalkyl, $C_2$-$C_4$alkenyl, $C_2$-$C_4$haloalkenyl, $C_2$-$C_4$alkynyl or $C_2$-$C_4$haloalkynyl.

More preferably still, $R^{11}$ is hydrogen, $C_1$-$C_2$alkyl, $C_1$-$C_2$haloalkyl, $C_2$-$C_3$alkenyl or $C_2$-$C_3$alkynyl. Yet even more preferably $R^{11}$ is hydrogen, methyl, ethyl, n-propyl, isopropyl, n-butyl, 2-methylpropyl, 2-fluoroethyl, 2,2-difluoroethyl, trifluoroethyl, allyl, but-3-en-1-yl or propargyl. Examples of such most preferred groups for $R^{11}$ are hydrogen, methyl, ethyl, 2,2-difluoroethyl, allyl and propargyl.

As stated herein, $A_3$ is either C(O) or S(O)$_2$. In one set of preferred embodiments $A_3$ is C(O). In another set of preferred embodiments $A_3$ is S(O)$_2$.

As stated herein $A_4$ is $CR^1$, $N(R^{13})_n$, O or S, and $A_5$ is $CR^2$, $N(R^{14})_n$, O or S. The value of n as applied to $R^{13}$ or $R^{14}$ is 0 or 1 and varies depending on the nature of $A_4$ and/or $A_5$: it is selected such that the 5-membered ring on the left-hand side of the bicyclic moiety remains aromatic in nature.

In one set of embodiments $A_4$ is $NR^{13}$ or N, whilst in a second set of embodiments $A_4$ is $CR^1$.

Preferably $R^1$ is selected from the group consisting of hydrogen $C_1$-$C_6$-alkyl, $C_1$-$C_3$-alkoxy, $C_1$-$C_3$alkoxy-$C_1$-$C_3$alkoxy-, $C_1$-$C_3$-alkylthio, $C_1$-$C_3$-alkylsulfonyl, $C_3$-$C_4$-cycloalkyl, $C_1$-$C_3$alkoxy-$C_1$-$C_3$-alkyl and $C_1$-$C_3$-alkylthio-$C_1$-$C_3$-alkyl. More preferably $R^1$ is selected from hydrogen, methyl, cyclopropyl, methoxy, ethoxy, —S-methyl, methylsulfonyl, and methoxyethoxy-. Most preferably $R^1$ is hydrogen.

Preferably $R^{13}$ is preferably hydrogen, methyl or $C_1$haloalkyl, more preferably hydrogen or methyl.

In a third set of embodiments $A_4$ is S, and in a fourth set of embodiments $A_4$ is O.

As stated above, $A_5$ is $CR^2$, $N(R^{14})_n$, O or S. In embodiments where $A_5$ is $CR^2$, $R^2$ is hydrogen, halogen, methyl or $C_1$haloalkyl however, it is particularly preferred that $R^2$ is hydrogen. In embodiments where $A_5$ is N or $NR^{14}$, it is preferred that $A_5$ is N or that $R^{14}$ is hydrogen or methyl, more preferably hydrogen.

In particularly preferred embodiments:
(i) $A_4$ is N or $NR^{13}$, and $A_5$ is S;
(ii) $A_4$ is N or $NR^{13}$ and $A_5$ is $CR^2$;
(iii) $A_4$ is $NR^{13}$ and $A_5$ is N;
(iv) $A_4$ is $CR^1$ and $A_5$ is N or $NR^{14}$;
(v) $A_4$ is $CR^1$ and $A_5$ is S;
(vi) $A_4$ is $CR^1$ and $A_5$ is CR2;
(vii) $A_4$ is $CR^1$ and $A_5$ is O;
(viii) $A_4$ is S and $A_5$ is N or $NR^{14}$;
(ix) $A_4$ is S and $A_5$ is $CR^2$;
(x) $A_4$ is O and $A_5$ is $CR^2$; and
(xi) $A_4$ is O and $A_5$ is N.

As described herein, G may be hydrogen or —C(O)—$R^3$, and $R^3$ is selected from the group consisting of $C_1$-$C_6$alkyl, $C_2$-$C_6$alkenyl, $C_2$-$C_6$alkynyl, $C_1$-$C_6$alkyl-S—, $C_1$-$C_6$alkoxy, —$NR^4R^5$ and phenyl optionally substituted by one or more $R^6$. As defined herein, $R^4$ and $R^5$ are independently selected from the group consisting of $C_1$-$C_6$ alkyl, $C_1$-$C_6$ alkoxy-; or they can together form a morpholinyl ring. Preferably $R^4$ and $R^5$ are each independently selected from the group consisting of methyl, ethyl, propyl, methoxy, ethoxy and propoxy. $R^6$ is selected from the group consisting of halogen, cyano, nitro, $C_1$-$C_3$alkyl, $C_1$-$C_3$haloalkyl, $C_1$-$C_3$alkoxy and $C_1$-$C_3$haloalkoxy.

Preferably $R^3$ is $C_1$-$C_4$ alkyl, $C_1$-$C_4$alkoxy, $C_2$-$C_3$alkenyl, $C_2$-$C_3$alkynyl, —$C_1$-$C_3$alkoxy, or —$NR^4R^5$ wherein $R^4$ and $R^5$ together form a morpholinyl ring. More preferably $R^3$ is isopropyl, t-butyl, methyl, ethyl, propargyl, methoxy, ethoxy or tert-butoxy.

In one set of embodiments G is hydrogen or —C(O)—$R^3$, wherein $R^3$ is $C_1$-$C_4$ alkyl, $C_2$-$C_3$alkenyl, $C_2$-$C_3$alkynyl or —$C_1$-$C_3$alkoxy. In a further set of embodiments G is hydrogen or —C(O)—$R^{3'}$ wherein $R^3$ is isopropyl, t-butyl, methyl, ethyl, propargyl or methoxy. However, it is particularly preferred that G is hydrogen.

As stated above T is a 5- or 6-membered monocyclic heteroaryl ring system containing 1, 2, or 3 heteroatoms independently selected from nitrogen, oxygen and sulphur, said 5-membered ring system being substituted by one or more radicals selected from X, Y, and $R^7$, and said 6-membered ring system being substituted by one or more radicals selected from $X^1$, $X^2$, $X^3$, $X^4$ and $R^7$, and wherein the oxy-alkyl-D moiety and the bi-cyclic moiety are linked via ring T such that they are situated ortho with respect to each other; or T is a substituted phenyl ring of formula (Tp)

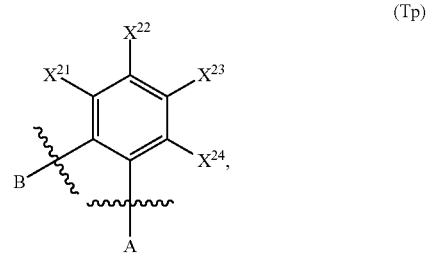

(Tp)

wherein $X^{21}$, $X^{22}$, $X^{23}$, $X^{24}$ are as defined herein.

Where T is a 5-membered monocyclic heteroaryl ring, it is preferably a furyl, thienyl, pyrrolyl, pyrazolyl, imidazolyl, triazolyl, oxazolyl, isoxazolyl, thiazolyl, isothiazolyl, or oxadiazolyl ring substituted by one or more radicals independently selected from X, Y and $R^7$. Where T is a 6-membered monocyclic heteroaryl ring, it is preferably a pyridyl, pyrimidinyl, pyridazinyl, pyrazinyl, or triazinyl ring, substituted by one or more radicals independently selected from $X^1$, $X^2$, $X^3$, $X^4$ and $R^7$. In each case, it is important that the oxy-alkyl-D moiety and group (B) are linked via ring T such that they are situated ortho with respect to each other.
For example, T may be selected from any one of (Tp) or (T1) to (T62) as shown below, wherein A denotes the point of attachment to the oxy-alkyl-D moiety and B denotes the point of attachment to group (B):
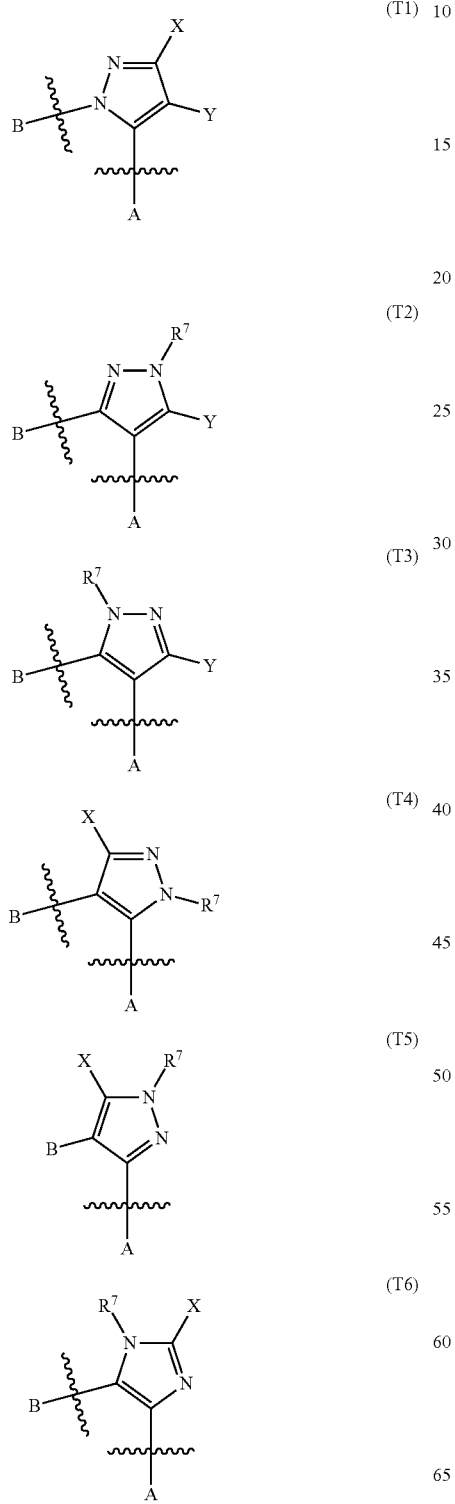
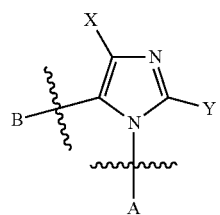
(T7)
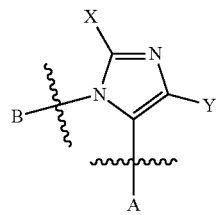
(T8)
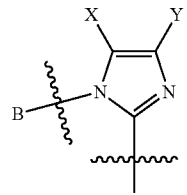
(T9)
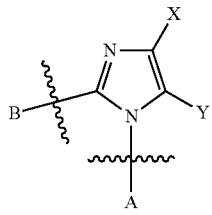
(T10)
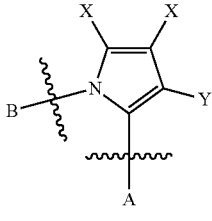
(T11)
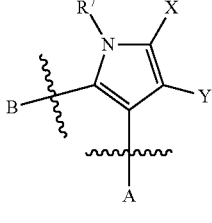
(T12)
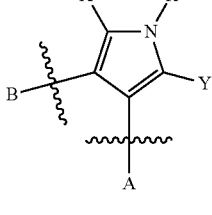
(T13)

-continued
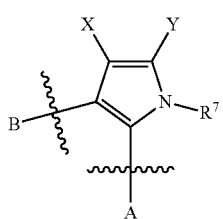 (T14)
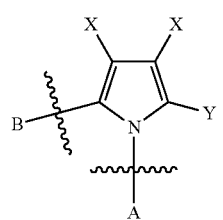 (T15)
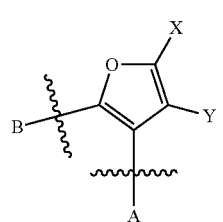 (T16)
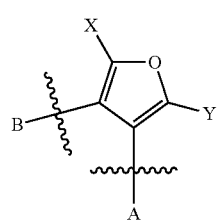 (T17)
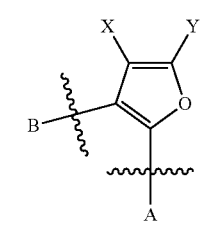 (T18)
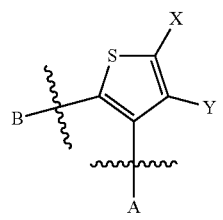 (T19)
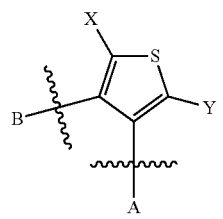 (T20)
-continued
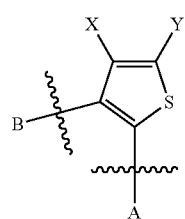 (T21)
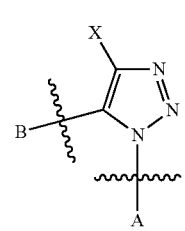 (T22)
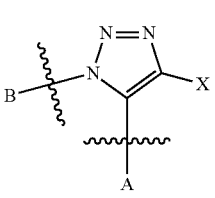 (T23)
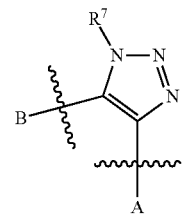 (T24)
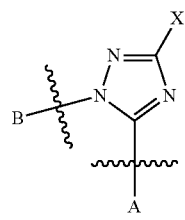 (T25)
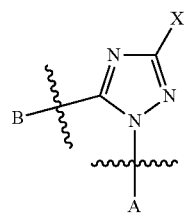 (T26)
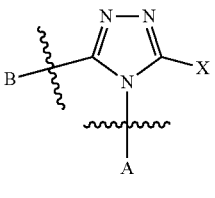 (T27)

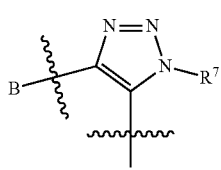 (T28)
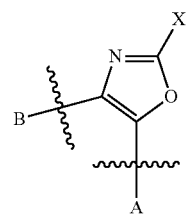 (T29)
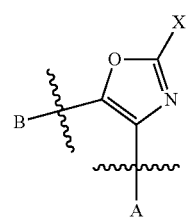 (T30)
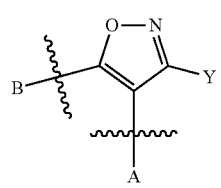 (T31)
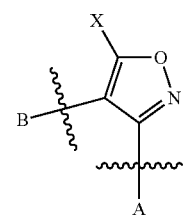 (T32)
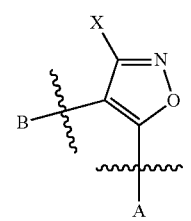 (T33)
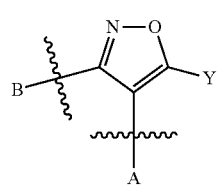 (T34)
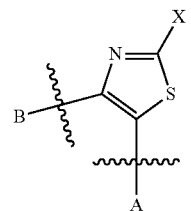 (T35)
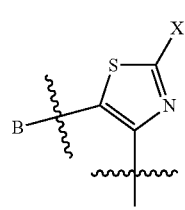 (T36)
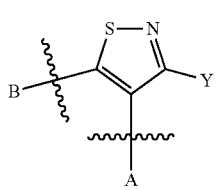 (T37)
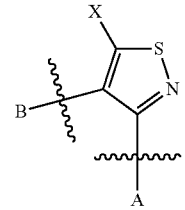 (T38)
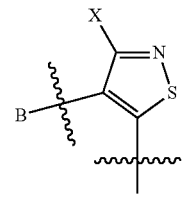 (T39)
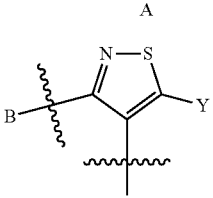 (T40)
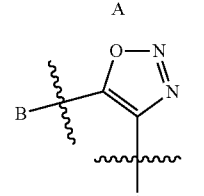 (T41)
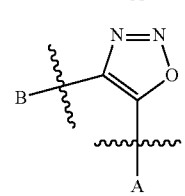 (T42)
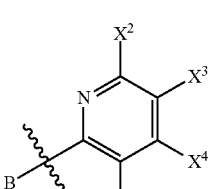 (T43)
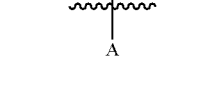

-continued
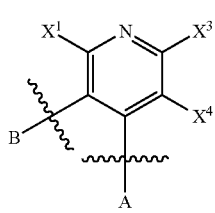 (T44)
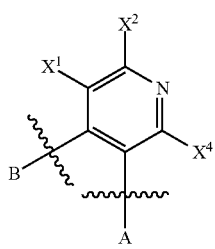 (T45)
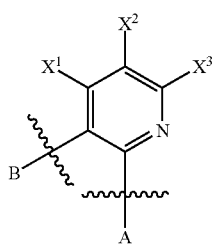 (T46)
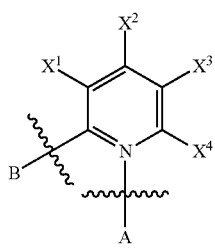 (T47)
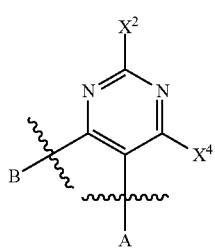 (T48)
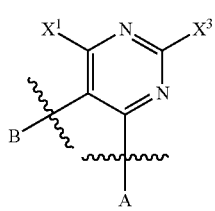 (T49)
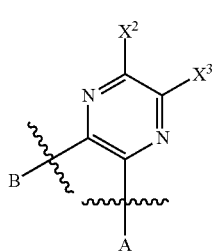 (T50)
-continued
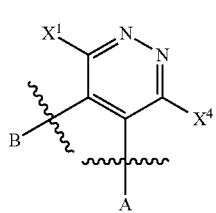 (T51)
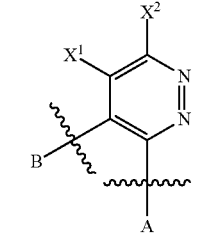 (T52)
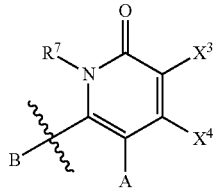 (T53)
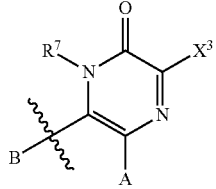 (T54)
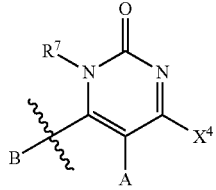 (T55)
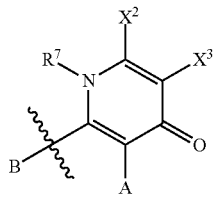 (T56)
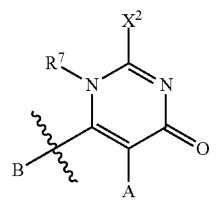 (T57)

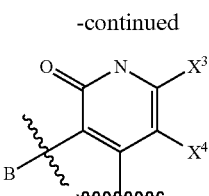
(T58)

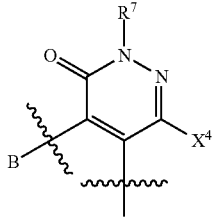
(T59)

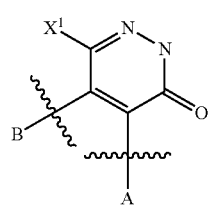
(T60)

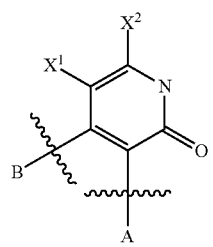
(T61)

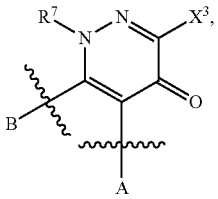
(T62)

wherein in X, $X^1$, $X^2$, $X^3$, $X^4$, Y, $R^7$, A and B are as defined herein.

In embodiments where T is (Tp), $X^{22}$ is preferably hydrogen; $X^{21}$ is preferably $C_1$-$C_3$ alkyl, $C_1$-$C_3$haloalkyl, or halogen, more preferably $C_1$-$C_3$alkyl, $C_1$haloalkyl, or halogen, even more preferably chloro, fluoro, bromo, methyl, or trifluoromethyl, and most preferably chloro, fluoro or trifluoromethyl. $X^{23}$ and $X^{24}$ are preferably independently hydrogen, $C_1$-$C_3$ alkyl, $C_1$-$C_3$haloalkyl, or halogen. Preferably $X^{24}$ is halogen, methyl or trfluoromethyl, more preferably chloro, fluoro, bromo, methyl or trifluoromethyl, and more preferably still, chloro.

In embodiments where T is a 5-membered monocyclic heteroaryl ring, and T bears more than one X radical, each is independently selected from hydrogen, $C_1$-$C_3$ alkyl, $C_1$-$C_3$ alkoxy, $C_1$-$C_3$haloalkyl, $C_1$-$C_3$haloalkoxy, or halogen. Where T bears an X substituent located ortho with respect to group (B), that X substituent is preferably $C_1$-$C_3$ alkyl, $C_1$-$C_3$ alkoxy, $C_1$-$C_3$haloalkyl, $C_1$-$C_3$haloalkoxy, or halogen.

More preferably where T contains an X substituent that is ortho with respect to group (B) [e.g. in (T4), (T5), (T7), (T8), (T9), (T11), (T13), (T14), (T15), (T17), (T18), (T20), (T21), (T22), (T32), (T33), (T37), and (T38)] it is independently halogen, more preferably fluoro, chloro, or bromo, and more preferably still, fluoro or chloro.

Where T contains an X substituent located meta to either group (B) or to the optionally substituted oxy-alkyl-D moiety [e.g. in (T1), (T6), (T10), (T11), (T12), (T15), (T16), (T19), (T25), (T26), (T29), (T30), (T35), and (T36)] each X is preferably, independently, hydrogen or halogen, more preferably hydrogen, fluoro, chloro, or bromo, and more preferably still, hydrogen, fluoro or chloro.

Where T contains a Y substituent, [e.g. in (T1), (T2), (T3), (T7), (T8), (T9), (T10), (T11), (T12), (T13), (T14), (T15), (T16), (T17), (T18), (T19), (T20), (T21), (T37), and (T40)] it is preferably hydrogen, $C_1$-$C_3$ alkyl, $C_1$-$C_3$haloalkyl, or halogen. More preferably Y is hydrogen, chloro, fluoro, or bromo.

Where T contains a $R^7$ substituent, [e.g. in (T2), (T3), (T4), (T5), (T6), (T12), (T13), (T14), (T24), and (T28)], which is a substituent borne on a free nitrogen of ring T (by "free nitrogen" it is meant a nitrogen within ring T which is not involved in linking ring T to either group (B) or to the oxy-alkyl-D moiety), it is preferably hydrogen, $C_1$-$C_3$ alkyl, or $C_1$-$C_3$haloalkyl. Where such an $R^7$ substituent is situated ortho with respect to group (B), it is preferably $C_1$-$C_3$ alkyl, or $C_1$-$C_3$haloalkyl, more preferably methyl or halomethyl.

In one set of embodiments, T is (Tp) or is an optionally substituted pyrazolyl ring selected from the group consisting of

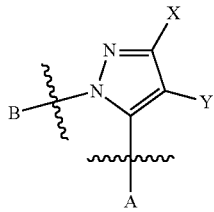
(T1)

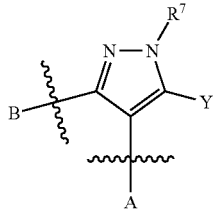
(T2)

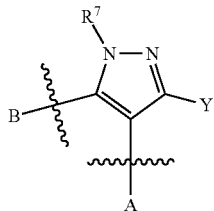
(T3)

-continued

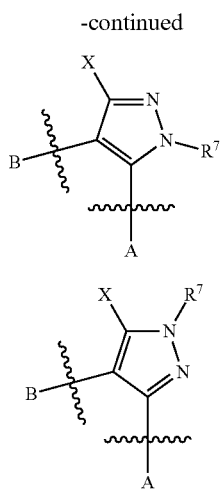

(T4)

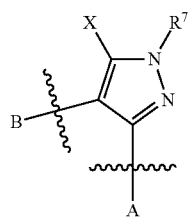

(T5)

wherein,

X and Y are each independently hydrogen, $C_1$-$C_3$ alkyl, $C_1$-$C_3$ alkoxy, $C_1$-$C_3$haloalkyl, $C_1$-$C_3$haloalkoxy, or halogen;

$R^7$ is hydrogen, $C_1$-$C_3$ alkyl, $C_1$-$C_3$ alkoxy, $C_1$-$C_3$haloalkyl, or $C_1$-$C_3$haloalkoxy, A denotes the point of attachment to the oxy-alkyl-D moiety and B denotes the point of attachment to the bi-cyclic moiety.

In embodiments where T is an optionally substituted pyrazolyl ring selected from the group consisting of (T1), (T2), (T3), (T4) and (T5), where T contains an X substituent, i.e. in (T1), (T4), and (T5), X is preferably hydrogen or halogen, more preferably hydrogen, fluoro, chloro, or bromo, and more preferably still, hydrogen, fluoro or chloro. More preferably in these embodiments, where X is situated ortho with respect to group (B), i.e. in (T4) and (T5), X is preferably halogen, more preferably, fluoro, chloro, or bromo, and more preferably still, fluoro or chloro.

Similarly in such embodiments, where T contains a Y substituent, i.e. in (T1), (T2), and (T3), Y is preferably hydrogen, $C_1$-$C_3$ alkyl, $C_1$-$C_3$haloalkyl, or halogen. More preferably Y is hydrogen, chloro, fluoro, or bromo. Similarly in such embodiments where T contains a $R^7$ substituent, i.e. in (T2), (T3), (T4), and (T5), which is a substituent borne on a free nitrogen of the pyrazolyl ring, $R^7$ is preferably $C_1$-$C_3$ alkyl, or $C_1$-$C_3$haloalkyl, more preferably methyl or halomethyl.

In one set of embodiments it is preferred that T is (T3) or (T4). In certain examples of these embodiments, $R^7$ is $C_1$-$C_3$ alkyl, preferably methyl or ethyl, more preferably methyl; Y is $C_1$-$C_3$ alkyl, preferably methyl or ethyl; and X is halogen, preferably bromo, chloro or fluoro, more preferably chloro.

In a further set of embodiments, T is a 6-membered monocyclic heteroaryl ring system containing 1, 2, or 3 heteroatoms independently selected from nitrogen, oxygen and sulphur, said 6-membered ring system being substituted by one or more radicals selected from $X^1$, $X^2$, $X^3$, $X^4$ and $R^7$. In such embodiments, T is preferably an optionally substituted pyridyl, pyrimidinyl, pyridazinyl, pyrazinyl, or triazinyl ring, more preferably selected from the group consisting of (T43), (T44), (T45), (T46), (T47), (T48), (T49), (T50), (T51), (T52), (T53), (T54), (T55), (T56), (T57), (T58), (T59), (T60), (T61), and (T62).

In such embodiments, $X^1$ is preferably oxo, $C_1$-$C_3$ alkyl, $C_1$-$C_3$haloalkyl, or halogen, more preferably $C_1$-$C_3$alkyl or halogen, and even more preferably chloro, fluoro, bromo, methyl, or trifluoromethyl. Similarly, $X^2$ and $X^4$ are each independently, preferably hydrogen, oxo, $C_1$-$C_3$alkyl, $C_1$-$C_3$haloalkyl or halogen, more preferably hydrogen or oxo. $X^3$ in such embodiments is preferably hydrogen, $C_1$-$C_3$alkyl, or $C_1$-$C_3$haloalkyl. In such embodiments $R^7$ is preferably hydrogen, $C_1$-$C_3$ alkyl, or $C_1$-$C_3$haloalkyl. Where $R^7$ is ortho with respect to group (B), it is more preferably $C_1$-$C_3$ alkyl, or $C_1$-$C_3$haloalkyl.

As described herein, D is the group (Dp) or is a substituted or unsubstituted 5- or 6-membered monocyclic heteroaryl ring containing 1, 2, or 3 heteroatoms independently selected from oxygen, nitrogen and sulphur, and wherein when D is substituted it is substituted on at least one ring carbon atom with $R^8$ and/or on a ring nitrogen atom with $R^9$. Where D is a substituted or unsubstituted 5- or 6-membered monocyclic heterocylclic ring, it is preferably a substituted (as described herein) or unsubstituted furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyridonyl, pyrimidinyl, pyridazinyl, pyrazinyl, 1,2,3-triazinyl, 1,2,4-triazinyl, or 1,3,5-triazinyl ring.

More preferably in such embodiments, D is a substituted (as described herein) or unsubstituted pyrazolyl, imidazolyl, oxazolyl, isoxazolyl, thiazolyl, isothiazolyl, pyridyl, pyridonyl, pyrimidinyl, pyridazinyl, or pyrazinyl ring.

More preferably still in such embodiments, D is a substituted (as described herein) or unsubstituted, oxazolyl, thiazolyl, or, pyridyl, ring.

Preferably each $R^8$ is independently oxo, $C_1$-$C_4$alkyl, $C_1$-$C_4$haloalkyl, halogen, cyano, hydroxyl, $C_1$-$C_4$alkoxy, or $C_1$-$C_4$alkylthio.

Preferably each $R^9$ is independently $C_1$-$C_4$alkyl, $C_1$-$C_4$haloalkyl, hydroxyl, $C_1$-$C_4$alkoxy, or $C_1$-$C_4$alkylthio.

However, as stated above D may alternatively be the group (Dp)

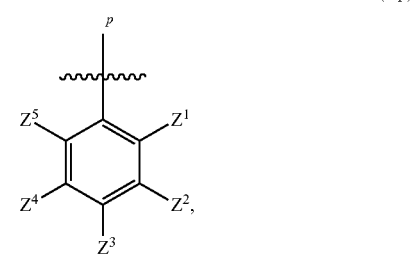

(Dp)

wherein $Z^1$, $Z^2$, $Z^3$, $Z^4$, and $Z^5$ are each independently selected from hydrogen, $C_1$-$C_3$ alkyl, $C_1$-$C_3$ alkoxy, $C_1$-$C_3$haloalkyl, $C_1$-$C_3$haloalkoxy, or halogen; and p is the point of attachment to the rest of the molecule.

Preferably $Z^1$, $Z^2$, $Z^3$, $Z^4$, and $Z^5$ are each independently selected from hydrogen, halogen (in particular chloro), methyl, methoxy, and trifluoromethyl.

In one set of embodiments each of $Z^1$, $Z^2$, $Z^4$, and $Z^5$ are hydrogen, and $Z^3$ is not hydrogen. Preferably in this set of embodiments, $Z^3$ is halogen, more preferably chloro.

In a further set of embodiments, each of $Z^1$, $Z^4$ and $Z^5$ are hydrogen, and $Z^2$ and $Z^3$ are not hydrogen. In this set of embodiments it is particularly preferred that $Z^2$ and $Z^3$ are each independently halogen, and more preferred that $Z^2$ and $Z^3$ are both chloro.

In one particularly preferred set of embodiments $Z^1$, $Z^2$, $Z^3$, $Z^4$ and $Z^5$ all carry hydrogen.

The compounds in Tables 1 to 17 below illustrate the compounds of the invention.

Table 1:

In Table X below, when X=1, Table 1 provides 21 compounds 1.01-1.21 of formula (I-iii), where D has the values listed in Table 1. Compounds of formula (I-iii) are examples of compounds of formula (I).

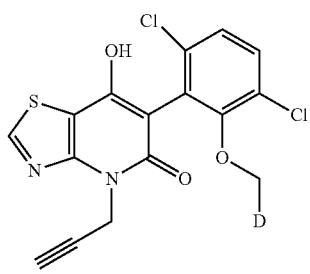

(I-iii)

Table 2:

In Table X below, when X=2, Table 2 provides 21 compounds 2.01-2.21 of formula (I-iv), where D has the values listed in Table 2. Compounds of formula (I-iv) are examples of compounds of formula (I).

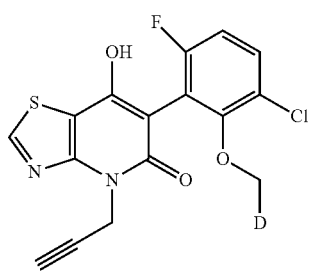

(I-iv)

Table 3:

In Table X below, when X=3, Table 3 provides 21 compounds 3.01-3.21 of formula (I-v), where D has the values listed in Table 3. Compounds of formula (I-v) are examples of compounds of formula (I).

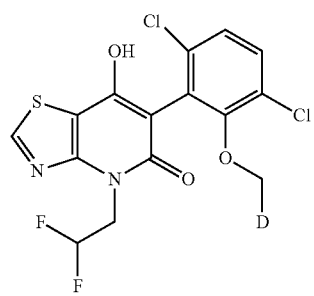

(I-v)

Table 4:

In Table X below, when X=4, Table 4 provides 21 compounds 4.01-4.21 of formula (I-vi), where D has the values listed in Table 4. Compounds of formula (I-vi) are examples of compounds of formula (I).

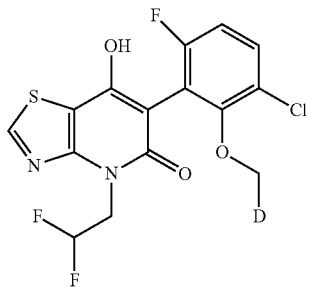

(I-vi)

Table 5:

In Table X below, when X=5, Table 5 provides 25 compounds of formula (I-vii), where D has the values listed in Table 5. Compounds of formula (I-vii) are examples of compounds of formula (I).

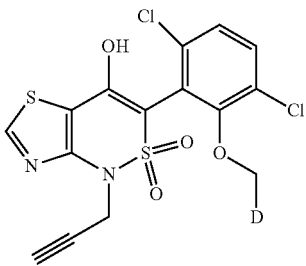

(I-vii)

Table 6:

In Table X below, when X=6, Table 6 provides 25 compounds of formula (I-viii), where D has the values listed in Table 6. Compounds of formula (I-viii) are examples of compounds of formula (I).

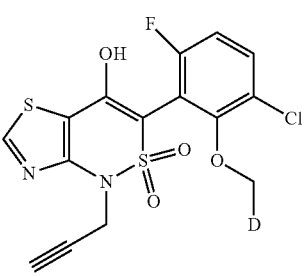

(I-viii)

Table 7:

In Table X below, when X=7, Table 7 provides 25 compounds of formula (I-ix), where D has the values listed in Table 7. Compounds of formula (I-ix) are examples of compounds of formula (I).

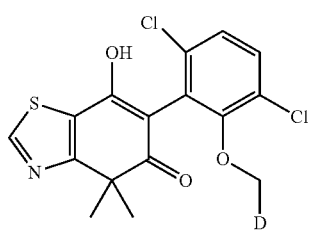

(I-ix)

Table 8:

In Table X below, when X=8, Table 8 provides 25 compounds of formula (I-x), where D has the values listed in Table 8. Compounds of formula (I-x) are examples of compounds of formula (I).

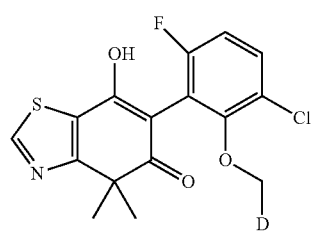

(I-x)

Table 9:

In Table X below, when X=9, Table 9 provides 25 compounds of formula (I-xi), where D has the values listed in Table 9. Compounds of formula (I-xi) are examples of compounds of formula (I).

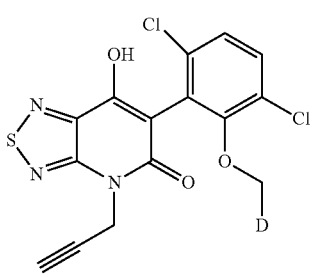

(I-xi)

Table 10:

In Table X below, when X=10, Table 10 provides 25 compounds of formula (I-xii), where D has the values listed in Table 10. Compounds of formula (I-xii) are examples of compounds of formula (I).

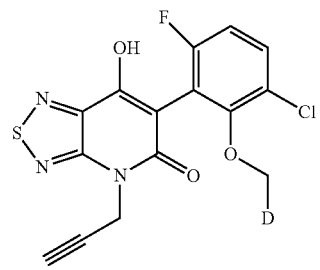

(I-xii)

Table 11:

In Table X below, when X=11, Table 11 provides 25 compounds of formula (I-xiii), where D has the values listed in Table 11. Compounds of formula (I-xiii) are examples of compounds of formula (I).

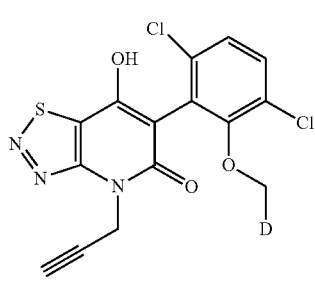

(I-xiii)

Table 12:

In Table X below, when X=12, Table 12 provides 25 compounds of formula (I-xiv), where D has the values listed in Table 12. Compounds of formula (I-xiv) are examples of compounds of formula (I).

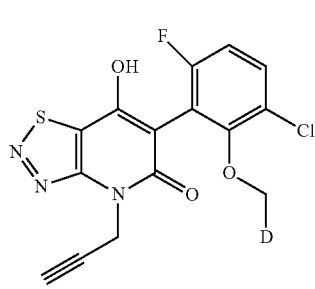

(I-xiv)

Table 13:

In Table X below, when X=13, Table 13 provides 25 compounds of formula (I-xv), where D has the values listed in Table 13. Compounds of formula (I-xv) are examples of compounds of formula (I).

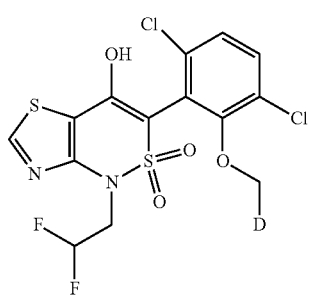

(I-xv)

Table 14:

In Table X below, when X=14, Table 14 provides 25 compounds of formula (I-xvi), where D has the values listed in Table 14. Compounds of formula (I-xvi) are examples of compounds of formula (I).

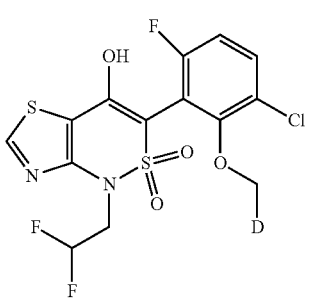

(I-xvi)

Table 15:

In Table X below, when X=15, Table 15 provides 25 compounds of formula (I-xvii), where D has the values listed in Table 15. Compounds of formula (I-xvii) are examples of compounds of formula (I).

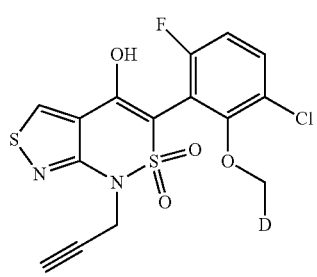

(I-xvii)

Table 16:

In Table X below, when X=16, Table 16 provides 25 compounds of formula (I-xviii), where D has the values listed in Table 16. Compounds of formula (I-xviii) are examples of compounds of formula (I).

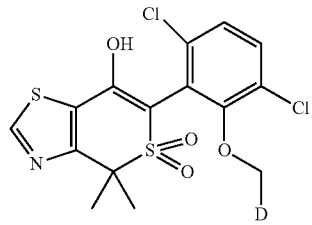

(I-xviii)

Table 17:

In Table X below, when X=17, Table 17 provides 25 compounds of formula (I-xix), where D has the values listed in Table 17. Compounds of formula (I-xix) are examples of compounds of formula (I).

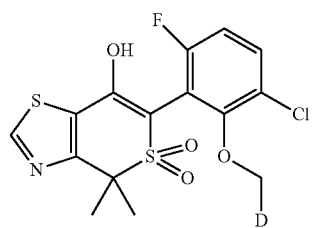

(I-xix)

TABLE X

X is an integer from 1-17 as defined above in Tables 1-17.

| Comp. No. | D |
|---|---|
| X.01 | 2-pyridyl- |
| X.02 | 3-pyridyl- |
| X.03 | 4-pyridyl- |
| X.04 | 2-thiazolyl- |
| X.05 | 4-thiazolyl- |
| X.06 | 5-thiazolyl- |
| X.07 | pyrazinyl- |
| X.08 | 2-pyrimidinyl- |
| X.09 | 4-pyrimidinyl- |
| X.10 | 5-pyrimidinyl- |
| X.11 | 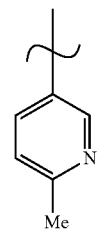 |
| X.12 | 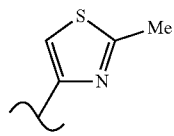 |
| X.13 | 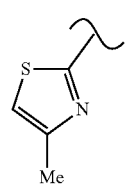 |

TABLE X-continued

X is an integer from 1-17 as defined above in Tables 1-17.

| Comp. No. | D |
|---|---|
| X.14 | 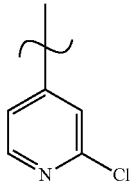 (2-chloropyridin-4-yl) |
| X.15 | 3-pyridazinyl- |
| X.16 | 4-pyridazinyl- |
| X.17 | 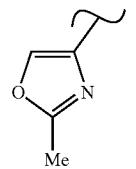 (2-methyloxazol-4-yl) |
| X.18 | 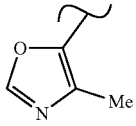 (4-methyloxazol-5-yl) |
| X.19 | 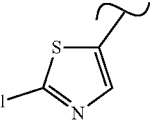 (2-chlorothiazol-5-yl) |
| X.20 | 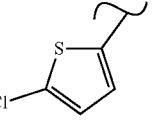 (5-chlorothiophen-2-yl) |
| X.21 | 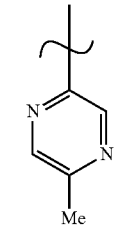 (5-methylpyrazin-2-yl) |
| X.22 | Phenyl- |
| X.23 | 4-chloro-phenyl- |
| X.24 | 4-fluoro-phenyl- |
| X.25 | 4-methoxy-phenyl- |

The compounds of the present invention may be prepared according to the following schemes, in which $A_3$, $A_4$, $A_5$, $R^{11}$, $X^{21}$, $X^{22}$, $X^{23}$, $X^{24}$, T and D have (unless otherwise stated explicitly) the definitions described hereinbefore.

Certain compounds (1) of the present invention may be prepared from compounds of formula (2) as shown in Reaction scheme 1. Compounds (1) are compounds of formula (I) in which G is hydrogen and $A_2$ is $NR^{11}$.

Since the processes described in Reaction scheme 1 and Reaction scheme 2 can on occasions be facilitated by the same combination of solvent and base, it is sometimes observed that attempted preparation of compounds of formula (2) according to Reaction scheme 2 gives compounds (1) of the present invention directly (a 'one pot' or 'telescoped' process).

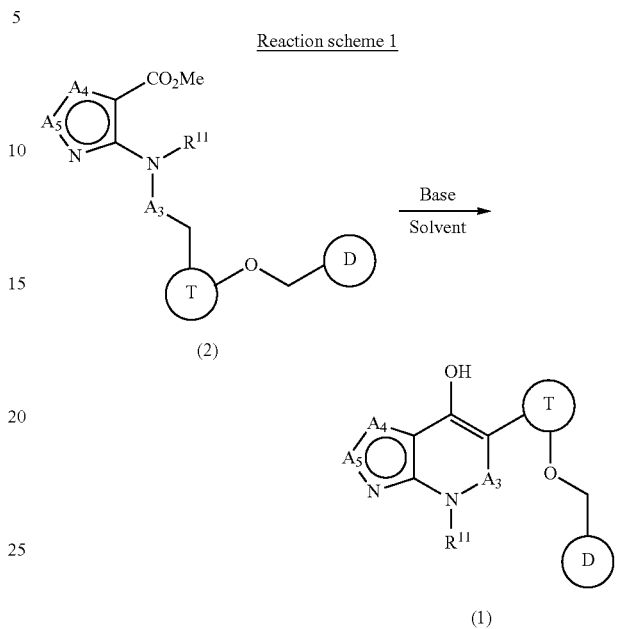

Reaction scheme 1

Compounds of formula (1) may be prepared by treatment of compounds (2) with a suitable base in a suitable solvent at a temperature between −10 and 50° C. Examples of suitable bases are sodium hydride, lithium hexamethyldisilazide, sodium hexamethyldisilazide or potassium hexamethyldisilazide. Examples of suitable solvents are acetonitrile, tetrahydrofuran or N,N-dimethylformamide.

Compounds of formula (2) may be prepared from compounds of formula (3) as shown in Reaction scheme 2.

Reaction scheme 2

Compounds of formula (2) may be prepared by N-alkylation of compounds (3) with an electrophilic alkylating agent, in the presence of a suitable base and solvent, at a temperature between 0 and 100° C. Examples of suitable electrophile reagents are propargyl bromide, methyl iodide, dimethyl sulfate or 2,2-difluoroethyl triflate. Examples of suitable bases are sodium hydride, lithium hexamethyldisilazide, sodium hexamethyldisilazide, potassium hexamethyldisilazide, diisopropylethylamine or potassium carbonate. Examples of suitable solvents are tetrahydrofuran, N,N-dimethylformamide or acetonitrile.

Compounds of formula (3) may be prepared by coupling of amino-heterocycles (5) with chlorides (4) as shown in Reaction scheme 3.

Reaction scheme 3

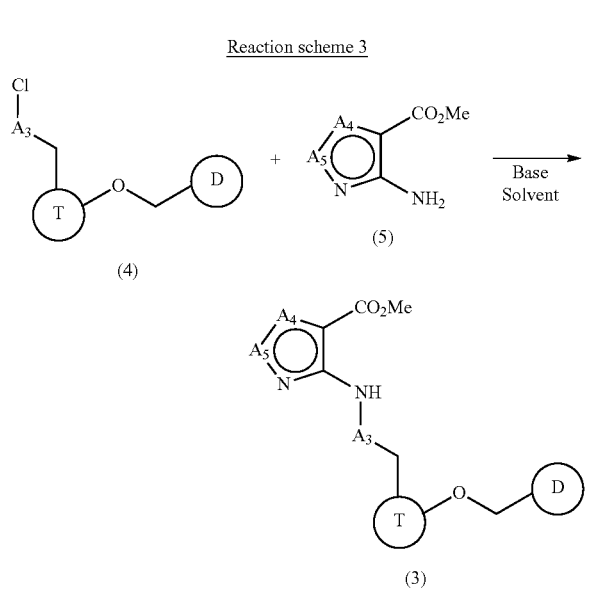

Compounds of formula (3) may be prepared by reacting chlorides (4) with amino-heterocycles (5), in the presence of a base [such as pyridine or triethylamine], in a suitable solvent. Examples of suitable solvents are dichloromethane, tetrahydrofuran or acetonitrile. Examples of compounds (4) are acyl chlorides (4-i), wherein $A_3$ is C(O), prepared according to Reaction Scheme 6. Further examples of compounds (4) are sulfonyl chlorides (4-ii), wherein $A_3$ is $S(O)_2$, prepared according to Reaction scheme 13. An example of amino-heterocycles (5) is amino-thiazole (5-i), prepared according to Reaction scheme 4 (a method which is known from PCT patent application WO2012/087976). Further examples of amino-heterocycles (5) may be prepared according to Reaction scheme 5.

Reaction scheme 4

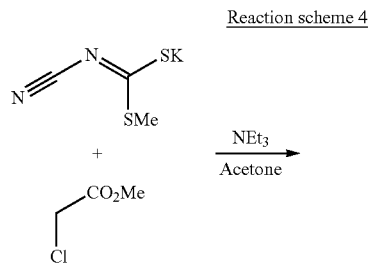

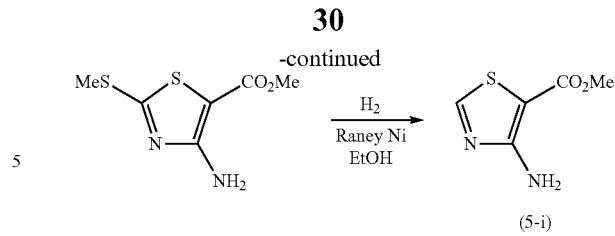

With reference to Reaction scheme 4, cyanimidodithiocarbonic acid monomethyl ester monopotassium salt is commercially available.

Reaction scheme 5

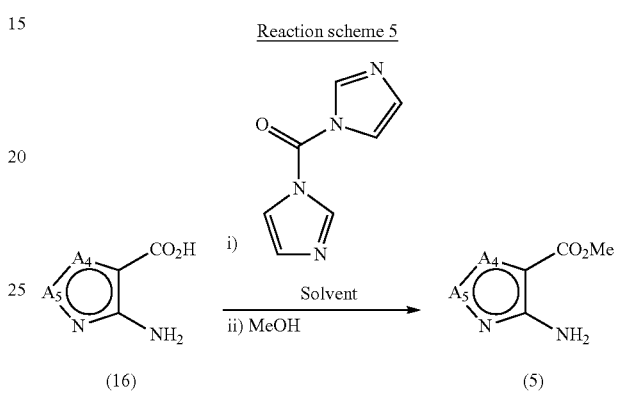

Amino-heterocycles of formula (5) may be prepared by treating amino-acids of formula (16) with 1,1'-carbonyldiimidazole then methanol, in a solvent [ethyl acetate, tetrahydrofuran, acetonitrile or mixtures thereof] at a temperature between −20° C. and 80° C. With reference to Reaction scheme 5, many amino-acids of formula (16) are commercially available. Examples are 4-amino-[1,2,5]thiadiazole-3-carboxylic acid and 3-aminoisothiazole-4-carboxylic acid.

Reaction scheme 6

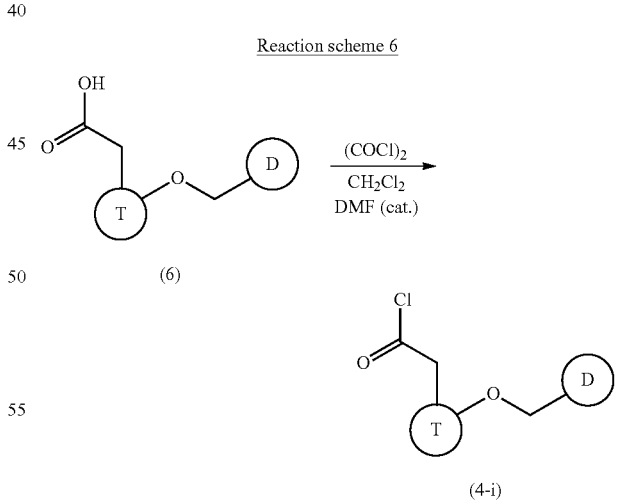

With reference to Reaction scheme 6, carboxylic acids (6) may be prepared by a variety of methods. Compounds of formula (6-i) are compounds of formula (6) in which T is a substituted phenyl ring of formula (Tp). Compounds (6-i) may be prepared as shown in Reaction scheme 7. Other carboxylic acids of formula (6) may be prepared as shown in Reaction scheme 11.

Reaction scheme 7

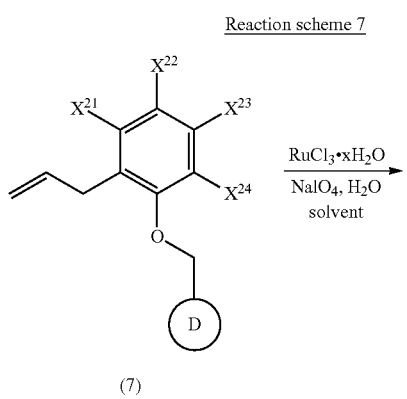

(7)

Compounds of formula (6-i) may be prepared by treatment of compounds (7) with ruthenium tetroxide, generated in situ from ruthenium trichloride hydrate and sodium periodate, in a solvent system containing water and one or more organic solvents from the list of ethyl acetate, dichloromethane or acetonitrile, at a temperature between 0 and 40° C.

Compounds of formula (7) may be prepared from phenols (8) as shown in Reaction scheme 8.

Reaction scheme 8

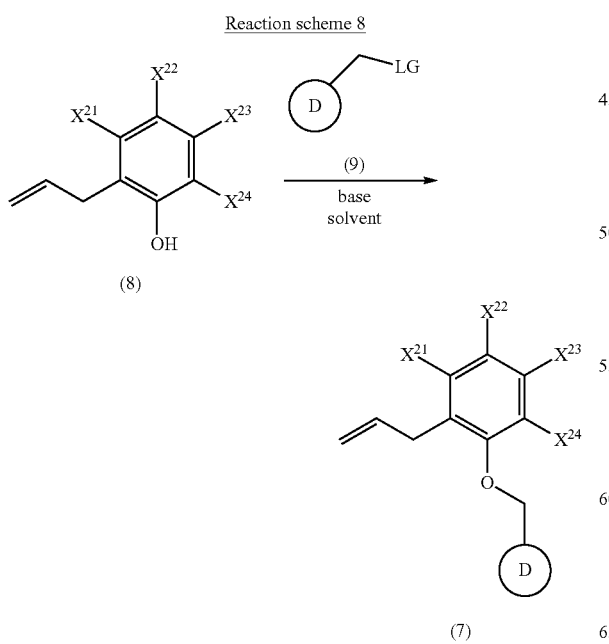

Compounds of formula (7) may be prepared by treatment of phenols (8) with alkylating agents of formula (9) [where LG is a leaving group such as chloride, bromide, iodide, mesylate or tosylate] in the presence of a suitable base and solvent at a temperature between 20 and 70° C. Examples of suitable bases are potassium carbonate, sodium hydroxide and triethylamine. Examples of suitable solvents are acetone, N,N-dimethylformamide, toluene and acetonitrile. Many alkylating agents of formula (9) or their salts are commercially available [such as 2-(bromomethyl)pyridine hydrobromide, 2-chloro-5-(chloromethyl)thiazole or benzyl bromide] or can be made by methods known to the skilled man.

Phenols (8) may be prepared as shown in Reaction scheme 9.

Reaction scheme 9

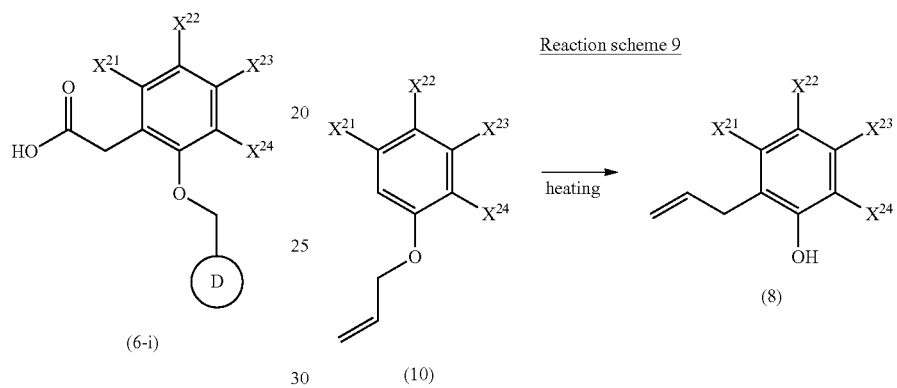

Phenols (8) may be prepared by heating compounds (10), optionally in the presence of a solvent [such as N,N-dimethylformamide or N,N-dimethylaniline], at a temperature between 180 and 220° C.

With reference to Reaction scheme 9, an example of compounds (10) is 2-allyloxy-1,4-dichloro-benzene, prepared according to *J. Chem. Soc., Perkin Trans.* 2, 2001, 1824. Other compounds of formula (10) may be synthesised similarly, according to Reaction scheme 10.

Reaction scheme 10

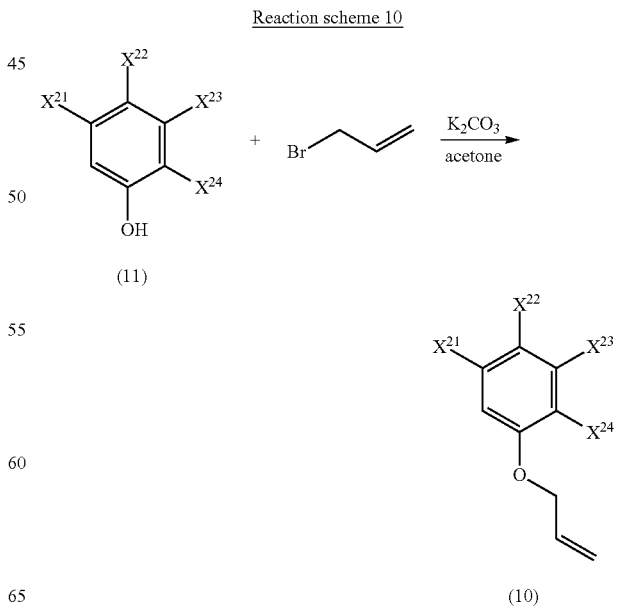

Compounds (10) may be prepared by treatment of phenols (11) with allyl bromide in the presence of potassium carbonate and acetone, at a temperature between 20 and 70° C.

With reference to Reaction scheme 10, many phenol compounds (11) are commercially available. Examples are 2,5-dichlorophenol and 2-chloro-5-fluorophenol.

Reaction scheme 11

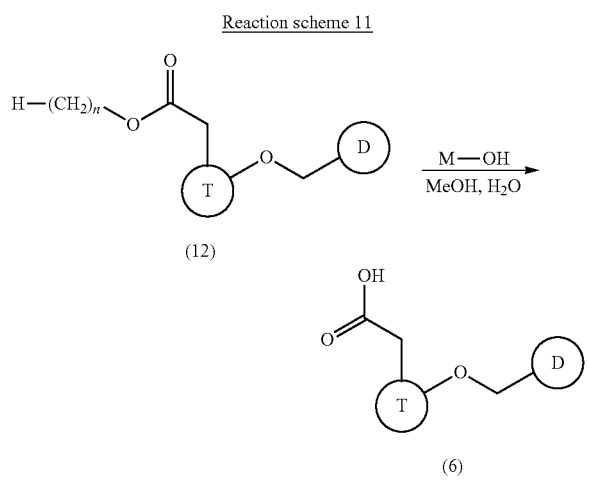

Carboxylic acids of formula (6) may be prepared by hydrolysis of esters (12) [where n=1 or 2] with an alkali metal hydroxide in a mixture of methanol and water at a temperature between 20 and 100° C. Examples of suitable alkali metal hydroxides are sodium hydroxide and potassium hydroxide.

Esters of formula (12) may be prepared from compounds (13) as shown in Reaction scheme 12.

Reaction scheme 12

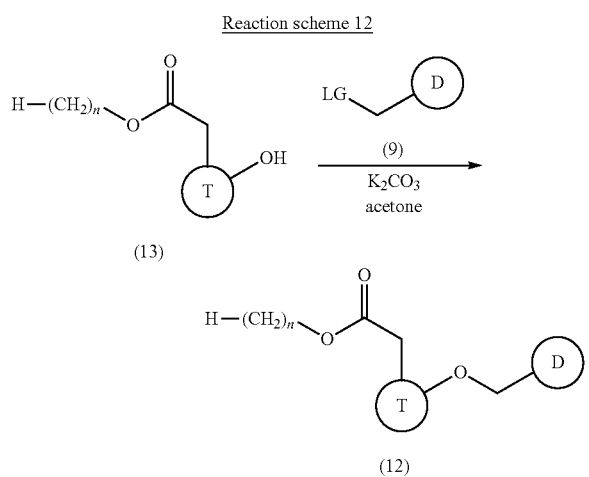

Esters (12) [where n=1 or 2] may be prepared by alkylation of phenols (13) [where n=1 or 2] with alkylating agents of formula (9) [where LG is a leaving group such as chloride, bromide, iodide, mesylate or tosylate] in the presence of potassium carbonate in acetone at a temperature between 20 and 70° C. Examples of phenols (13) are ethyl (5-hydroxy-1-methyl-1H-pyrazol-4-yl)acetate [prepared according to PCT patent application WO03/099793] and methyl α-(1,3-dimethyl-4-hydroxy-1H-pyrazol-5-yl)acetate [prepared according to European patent application EP0702005]. Other phenols (13) may be prepared according to Reaction scheme 16.

Reaction scheme 13

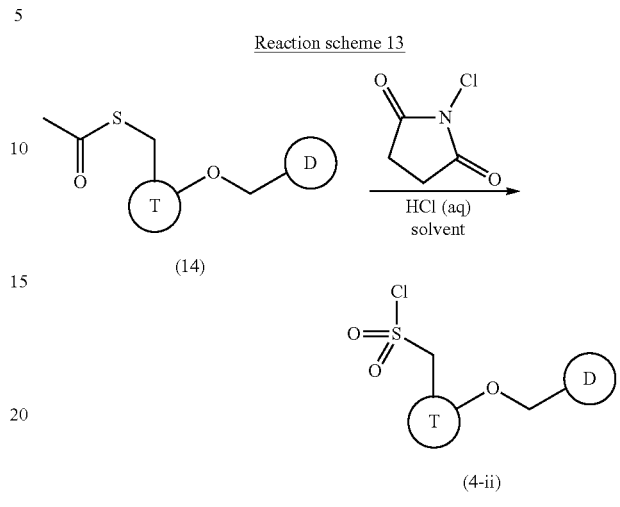

Sulfonyl chlorides (4-ii) may be prepared by treatment of thioacetates of formula (14) with N-chloro-succinimide (NCS) and hydrochloric acid in a suitable solvent [such as acetonitrile or tetrahydrofuran], as shown in Reaction scheme 13. Thioacetates of formula (14) are made according to Reaction scheme 14.

Reaction scheme 14

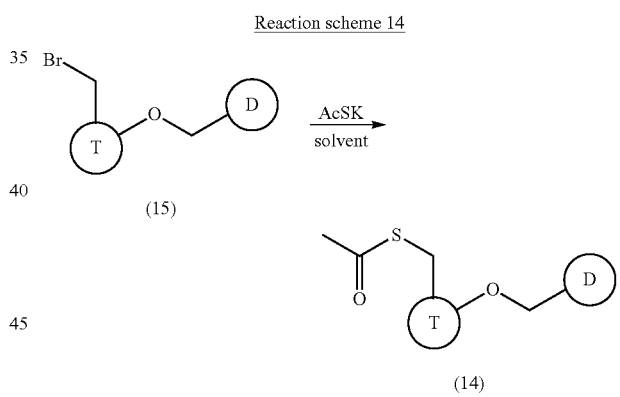

Thioacetates of formula (14) may be prepared by reaction of bromides (15) with potassium thioacetate in a suitable solvent [such as acetone or ethanol], optionally using heating. Bromides of formula (15) are prepared according to Reaction scheme 15.

Reaction scheme 15

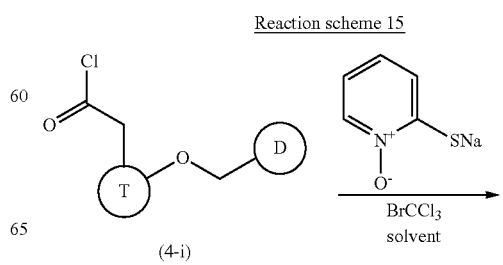

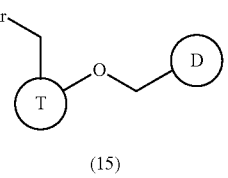

(15)

Bromides of formula (15) may be prepared by treating acyl chlorides (4-i) with bromotrichloromethane and 2-mercaptopyridine N-oxide sodium salt, in a suitable solvent [such as dichloromethane, chloroform or carbon tetrachloride], optionally using heating and optionally irradiating the reaction with UV light, as shown in Reaction scheme 15. Acyl chlorides (4-i) are prepared according to Reaction scheme 6.

Reaction scheme 16

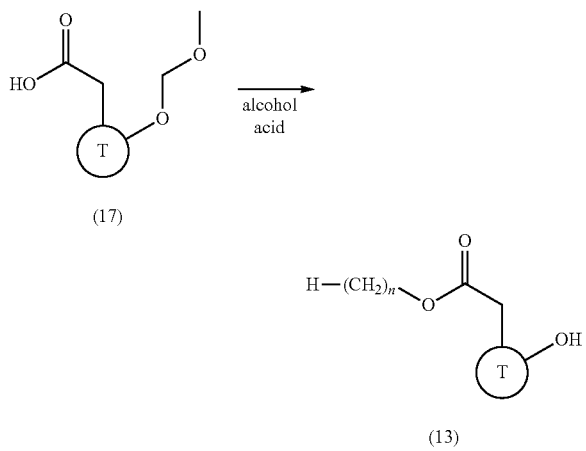

(17)

(13)

Phenols (13) [where n=1 or 2] may be prepared by treatment of compounds of formula (17) with an alcohol [specifically methanol where n=1 or ethanol where n=2] and an acid [such as sulfuric acid or hydrochloric acid] at a temperature between −10° C. and 120° C. Compounds of formula (17) are prepared according to Reaction scheme 17.

Reaction scheme 17

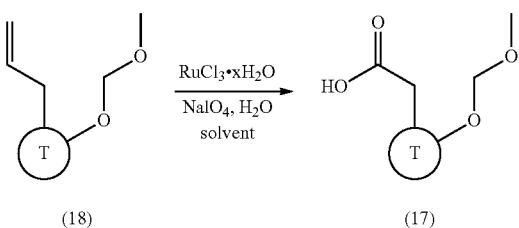

(18) (17)

Compounds of formula (17) may be prepared by treatment of compounds (18) with ruthenium tetroxide, generated in situ from ruthenium trichloride hydrate and sodium periodate, in a solvent system containing water and one or more organic solvents from the list of ethyl acetate, dichloromethane or acetonitrile, at a temperature between 0 and 40° C. Examples of compounds (18) are compounds of formula (18-i), where T is Tp, and the allyl moiety is ortho with respect to the methoxymethoxy moiety. Compounds of formula (18-i) are made according to Reaction scheme 18.

Reaction scheme 18

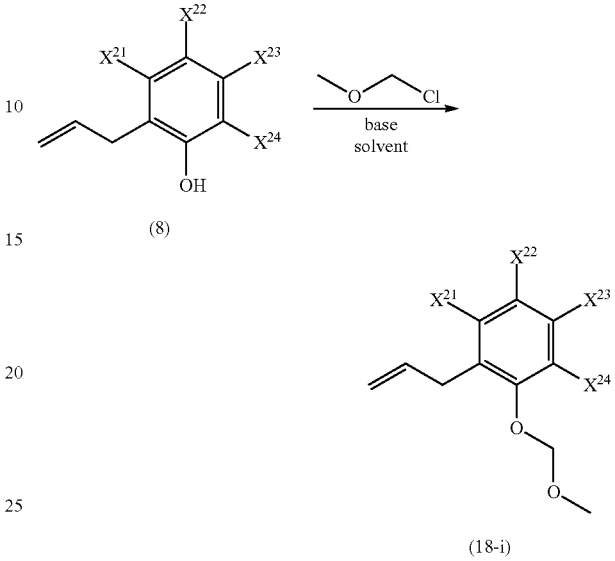

(8)

(18-i)

Compounds of formula (18-i) can be made by alkylation of phenols (8) with chloromethyl methyl ether in the presence of a base [such as sodium hydride or potassium carbonate] and a solvent [such as tetrahydrofuran, acetone or ethanol] at a temperature between −20° C. and 100° C. Phenols (8) are made according to Reaction scheme 9.

The compounds according to the invention can be used as herbicidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance. The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%

Dusts:
active ingredient: 0.1 to 10%, preferably 0.1 to 5%
solid carrier: 99.9 to 90%, preferably 99.9 to 99%

Suspension Concentrates:
active ingredient: 5 to 75%, preferably 10 to 50%
water: 94 to 24%, preferably 88 to 30%
surface-active agent: 1 to 40%, preferably 2 to 30%

Wettable Powders:
active ingredient: 0.5 to 90%, preferably 1 to 80%
surface-active agent: 0.5 to 20%, preferably 1 to 15%
solid carrier: 5 to 95%, preferably 15 to 90%

Granules:
active ingredient: 0.1 to 30%, preferably 0.1 to 15%
solid carrier: 99.5 to 70%, preferably 97 to 85%

The following Examples further illustrate, but do not limit, the invention:

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

The composition of the present may further comprise at least one additional pesticide. For example, the compounds according to the invention can also be used in combination with other herbicides or plant growth regulators. In a preferred embodiment the additional pesticide is a herbicide and/or herbicide safener.

Thus, compounds of formula (I) can be used in combination with one or more other herbicides to provide various herbicidal mixtures. Specific examples of such mixtures include (wherein "I" represents a compound of formula (I)):—I+acetochlor; I+aciflurofen-sodium; I+aclonifen; I+alachlor; I+alloxydim; I+ametryn; I+amicarbazone; I+amidosulfuron; I+aminocyclopyrachlor; I+aminopyralid; I+amitrole; I+asulam; I+atrazine; I+bensulfuron-methyl; I+bentazone; I+bicyclopyrone; I+bifenox; I+bispyribac-sodium; I+bromacil; I+bromoxynil; I+butafenacil; I+cafenstrole; I+carfentrazone-ethyl; I+chlorimuron-ethyl; I+chlorotoluron; I+cinosulfuron; I+clethodim; I+clodinafop-propargyl; I+clomazone; I+clopyralid; I+cyhalofop-butyl; I+2,4-D (including the choline salt and 2-ethylhexyl ester thereof); I+daimuron; I+desmedipham; I+dicamba (including the aluminum, aminopropyl, bis-aminopropylmethyl, choline, diglycolamine, dimethylamine, dimethylammonium, potassium and sodium salts thereof); I+diclofop-methyl; I+difenzoquat; I+diflufenican; I+diflufenzopyr; I+dimethachlor; I+dimethenamid-P; I+diquat dibromide; I+diuron; I+esprocarb; I+ethofumesate; I+fenoxaprop-P-ethyl; I+fenquinotrione; I+flazasulfuron; I+florasulam; I+fluazifop-P-butyl; I+flucarbazone-sodium; I+flufenacet; I+flumetralin; I+flumetsulam; I+flumioxazin; I+flupyrsulfuron-methyl-sodium; I+fluroxypyr-meptyl; I+fluthiacet-methyl; I+fomesafen; I+foramsulfuron; I+glufosinate (including the ammonium salt thereof); I+glyphosate (including the diammonium, isopropylammonium and potassium salts thereof); I+halauxifen-methyl; I+halosulfuron-methyl; I+haloxyfop-methyl; I+hexazinone; I+imazamox; I+imazapic; I+imazapyr; I+imazaquin; I+imazethapyr; I+indaziflam; I+iodosulfuron-methyl-sodium; I+iofensulfuron; I+iofensulfuron-sodium; I+ioxynil; I+ipfencarbazone; I+isoxaben; I+isoxaflutole; I+lactofen; I+linuron; I+mecoprop-P; I+mefenacet; I+mesosulfuron; I+mesosulfuron-methyl; I+mesotrione; I+metamitron; I+metobromuron; I+metolachlor; I+metoxuron; I+metribuzin; I+metsulfuron; I+molinate; I+napropamide; I+nicosulfuron; I+norflurazon; I+orthosulfamuron; I+oxadiargyl; I+oxadiazon; I+oxyfluorfen; I+paraquat dichloride; I+pendimethalin; I+penoxsulam; I+phenmedipham; I+picloram; I+picolinafen; I+pinoxaden; I+pretilachlor; I+primisulfuron-methyl; I+prodiamine; I+prometryn; I+propachlor; I+propanil; I+propaquizafop; I+propham; I+propyzamide; I+prosulfocarb; I+prosulfuron; I+pyrasulfotole; I+pyrazolynate, I+pyrazosulfuron-ethyl; I+pyribenzoxim; I+pyridate; I+pyriftalid; I+pyrithiobac-sodium; I+pyroxasulfone; I+pyroxsulam; I+quinclorac; I+quizalofop-P-ethyl; I+rimsulfuron; I+saflufenacil; I+sethoxydim; I+S-metolachlor; I+sulcotrione; I+sulfentrazone; I+tebuthiuron; I+tefuryltrione; I+tembotrione; I+terbuthylazine; I+terbutryn; I+thiencarbazone; I+thifensulfuron; I+tiafenacil; I+tolpyralate; I+topramezone; I+tralkoxydim; I+triafamone; I+triasulfuron; I+tribenuron-methyl; I+triclopyr; I+trifloxysulfuron-sodium; I+trifludimoxazin and tritosulfuron.

Especially preferred examples of such mixtures include: —I+ametryn; I+atrazine; I+bicyclopyrone; I+butafenacil; I+chlorotoluron; I+clodinafop-propargyl; I+clomazone; I+2,4-D (including the choline salt and 2-ethylhexyl ester thereof); I+dicamba (including the aluminum, aminopropyl, bis-aminopropylmethyl, choline, diglycolamine, dimethylamine, dimethylammonium, potassium and sodium salts thereof); I+dimethachlor; I+diquat dibromide; I+fluazifop-P-butyl; I+flumetralin; I+fomesafen; I+glufosinate-ammonium; I+glyphosate (including the diammonium, isopropylammonium and potassium salts thereof); I+mesotrione; I+molinate; I+napropamide; I+nicosulfuron; I+paraquat dichloride; I+pinoxaden; I+pretilachlor; I+primisulfuron-methyl; I+prometryn; I+prosulfocarb; I+prosulfuron; I+pyridate; I+pyriftalid; I+pyrazolynate, I+S-metolachlor; I+terbuthylazine; I+terbutryn; I+tralkoxydim; I+triasulfuron and I+trifloxysulfuron-sodium.

Preferred herbicide mixture products for weed control in cereals (especially wheat and/or barley) include: —I+amidosulfuron; I+aminopyralid; I+bromoxynil; I+carfentrazone-ethyl; I+chlorotoluron; I+clodinafop-propargyl; I+clopyralid; I+2,4-D (including the choline salt and 2-ethylhexyl ester thereof); I+dicamba (including the aluminum, aminopropyl, bis-aminopropylmethyl, choline, diglycolamine, dimethylamine, dimethylammonium, potassium and sodium salts thereof); I+difenzoquat; I+diflufenican; I+fenoxaprop-P-ethyl; I+florasulam; I+flucarbazone-sodium; I+flufenacet; flupyrsulfuron-methyl-sodium; I+fluroxypyr-meptyl; I+halauxifen-methyl; I+iodosulfuron-methyl-sodium; I+iofensulfuron; I+iofensulfuron-sodium; I+mesosulfuron; I+mesosulfuron-methyl; I+metsulfuron; I+pendimethalin; I+pinoxaden; I+prosulfocarb; I+pyrasulfotole; I+pyroxasulfone; I+pyroxsulam; I+topramezone; I+tralkoxydim; I+triasulfuron and I+tribenuron-methyl.

Preferred herbicide mixture products for weed control in corn include: —I+acetochlor; I+alachlor; I+atrazine; I+bicyclopyrone; I+2,4-D (including the choline salt and 2-ethylhexyl ester thereof); I+dicamba (including the aluminum, aminopropyl, bis-aminopropylmethyl, choline, diglycolamine, dimethylamine, dimethylammonium, potassium and sodium salts thereof); I+diflufenzopyr; I+dimethenamid-P; I+flumioxazin; I+fluthiacet-methyl; I+foramsulfuron; I+glufosinate (including the ammonium salt thereof); I+glyphosate (including the diammonium, isopropylammonium and potassium salts thereof); I+isoxaflutole; I+mesotrione; I+nicosulfuron; I+primisulfuron-methyl; I+prosulfuron; I+pyroxasulfone; I+rimsulfuron; I+S-metolachlor, I+terbutylazine; I+tembotrione; I+thiencarbazone and I+thifensulfuron.

Preferred herbicide mixture products for weed control in rice include: —I+2,4-D; I+2,4-D choline salt; I+2,4-D-2-ethylhexyl ester; I+bensulfuron-methyl; I+bispyribac-sodium; I+cafenstrole; I+cinosulfuron; I+clomazone; I+cyhalofop-butyl; I+daimuron; I+dicamba (including the aluminum, aminopropyl, bis-aminopropylmethyl, choline, diglycolamine, dimethylamine, dimethylammonium, potassium and sodium salts thereof); I+esprocarb; I+fenoxaprop-P-ethyl; I+florasulam; I+halauxifen-methyl; I+halosulfuron-methyl; I+iofensulfuron; I+ipfencarbazone; I+mefenacet; I+mesotrione; I+metsulfuron; I+molinate; I+orthosulfamuron; I+oxadiargyl; I+oxadiazon; I+pendimethalin; I+penoxsulam; I+pretilachlor; I+pyrazolynate, I+pyrazosulfuron-ethyl; I+pyribenzoxim; I+pyriftalid; I+quinclorac; I+tefuryltrione; I+triafamone and I+triasulfuron.

Preferred herbicide mixtures for weed control in soybean include: —I+acifluorfen-sodium; I+ametryn; I+atrazine; I+bentazone; I+bicyclopyrone; I+bromoxynil; I+carfentrazone-ethyl; I+chlorimuron-ethyl; I+clethodim; I+clomazone; I+2,4-D (including the choline salt and 2-ethylhexyl ester thereof); I+dicamba (including the aluminum, aminopropyl, bis-aminopropylmethyl, choline, diglycolamine, dimethylamine, dimethylammonium, potassium and sodium salts thereof); I+diquat dibromide; I+diuron; I+fenoxaprop-P-ethyl; I+fluazifop-P-butyl; I+flufenacet; I+flumioxazin; I+fomesafen; I+glufosinate (including the ammonium salt thereof); I+glyphosate (including the diammonium, isopropylammonium and potassium salts thereof); I+imazethapyr; I+lactofen; I+mesotrione; I+metolachlor; I+metribuzin; I+nicosulfuron; I+oxyfluorfen; I+paraquat dichloride; I+pendimethalin; I+pyroxasulfone; I+quizalofop-P-ethyl; I+saflufenacil; I+sethoxydim; I+S-metolachlor and I+sulfentrazone.

The mixing partners of the compound of Formula (I) may also be in the form of esters or salts, as mentioned e.g. in The Pesticide Manual, Fourteenth Edition, British Crop Protection Council, 2006.

The compound of Formula (I) can also be used in mixtures with other agrochemicals such as fungicides, nematicides or insecticides, examples of which are given in The Pesticide Manual.

The mixing ratio of the compound of Formula (I) to the mixing partner is preferably from 1:100 to 1000:1.

The mixtures can advantageously be used in the above-mentioned formulations (in which case "active ingredient" relates to the respective mixture of compound of Formula I with the mixing partner).

Compounds of formula (I) of the present invention may also be combined with herbicide safeners. Preferred combinations (wherein "I" represents a compound of Formula (I)) include: —I+benoxacor, I+cloquintocet-mexyl; I+cyprosulfamide; I+dichlormid; I+fenchlorazole-ethyl; I+fenclorim; I+fluxofenim; I+furilazole I+isoxadifen-ethyl; I+mefenpyr-diethyl; I+N-(2-methoxybenzoyl)-4-[(methylaminocarbonyl)amino] benzenesulfonamide and I+oxabetrinil.

Particularly preferred are mixtures of a compound of Formula I with cyprosulfamide, isoxadifen-ethyl, cloquintocet-mexyl and/or N-(2-methoxybenzoyl)-4-[(methylaminocarbonyl)amino]benzenesulfonamide.

The safeners of the compound of formula (I) may also be in the form of esters or salts, as mentioned e.g. in The Pesticide Manual, 14$^{th}$ Edition (BCPC), 2006. The reference to cloquintocet-mexyl also applies to a lithium, sodium, potassium, calcium, magnesium, aluminium, iron, ammonium, quaternary ammonium, sulfonium or phos-phonium salt thereof as disclosed in WO 02/34048, and the reference to fenchlorazole-ethyl also applies to fenchlorazole, etc.

Preferably the mixing ratio of compound of Formula (I) to safener is from 100:1 to 1:10, especially from 20:1 to 1:1.

The mixtures can advantageously be used in the above-mentioned formulations (in which case "active ingredient" relates to the respective mixture of compound of Formula (I) with the safener).

The compounds of formula (I) of this invention are useful as herbicides. The present invention therefore further comprises a method for controlling unwanted plants comprising applying to the said plants or a locus comprising them, an effective amount of a compound of the invention or a herbicidal composition containing said compound. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula (I) may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula (I) according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. In a particularly preferred aspect, the crop plant has been engineered to overexpress homogentisate solanesyltransferase as taught in, for example, WO2010/029311.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

Compounds of formula I and compositions of the invention can typically be used to control a wide variety of monocotyledonous and dicotyledonous weed species. Examples of monocotyledonous species that can typically be controlled include *Alopecurus myosuroides, Avena fatua, Brachiaria plantaginea, Bromus tectorum, Cyperus esculentus, Digitaria sanguinalis, Echinochloa crus-galli, Lolium perenne, Lolium multiflorum, Panicum miliaceum, Poa annua, Setaria viridis, Setaria faberi* and *Sorghum bicolor*. Examples of dicotyledonous species that can be controlled include *Abutilon theophrasti, Amaranthus retroflexus, Bidens pilosa, Chenopodium album, Euphorbia heterophylla, Galium aparine, Ipomoea hederacea, Kochia scoparia, Polygonum convolvulus, Sida spinosa, Sinapis arvensis, Solanum nigrum, Stellaria media, Veronica persica* and *Xanthium strumarium*.

Various aspects and embodiments of the present invention will now be illustrated in more detail by way of example. It will be appreciated that modification of detail may be made without departing from the scope of the invention.

PREPARATION EXAMPLES

Example 1 Preparation of 6-[3,6-dichloro-2-[(2-chlorothiazol-5-yl)methoxy]phenyl]-7-hydroxy-4-prop-2-ynyl-thiazolo[4,5-b]pyridin-5-one

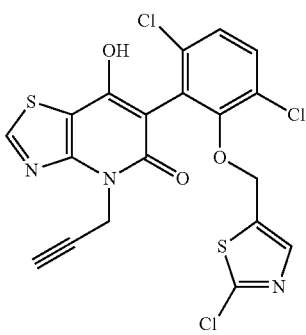 [SMILES: C#CCn1c(=O)c(-c2c(Cl)ccc(Cl)c2OCc2cnc(Cl)s2)c(O)c2scnc21]

1.1 2-allyloxy-1,4-dichloro-benzene

To a stirred solution of 2,5-dichlorophenol (50 g, 307 mmol) in acetone (300 mL) under $N_2$ was added potassium carbonate (42.4 g, 337 mmol) and the mixture stirred at room temperature for 10 min. Allyl bromide (41 g, 337 mmol) was added and the reaction heated at 60° C. for 4 h. The mixture was cooled to RT and filtered, the residue washed with acetone (300 ml) and the combined filtrate was concentrated under reduced pressure to afford 2-allyloxy-1, 4-dichloro-benzene as yellow oil (60 g, 96%) which was progressed without further purification.

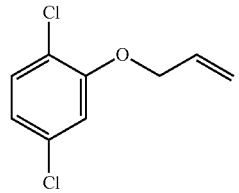

$^1$H NMR (400 MHz, CDCl$_3$): δ: 7.27 (d, J=8.3, 1H), 6.89-6.86 (m, 2H), 6.09-5.99 (m, 1H), 5.46 (d, J=17.3, 1H), 5.33 (d, J=10.6, 1H), 4.59 (d, J=4.9, 2H).

1.2 2-allyl-3,6-dichloro-phenol

A stirred solution of 2-allyloxy-1,4-dichloro-benzene (60 g, 295 mmol) in N,N-dimethylaniline (200 ml) was heated at 190-200° C. for 18 h. The reaction mixture was cooled to room temperature, poured into 30% hydrochloric acid (200 ml) and extracted with ethyl acetate (3×200 ml). The combined organics were washed with 30% hydrochloric acid (100 ml×4), followed by water and finally brine. The organics were dried over Na$_2$SO$_4$, filtered and concentrated to give 2-allyl-3,6-dichloro-phenol (58 g, 96%).

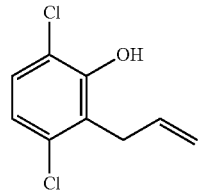

$^1$H NMR (400 MHz, CDCl$_3$): δ: 9.69 (s, 1H), 7.27 (d, J=8.6, 1H), 6.96 (d, J=8.6, 1H), 5.9-5.8 (m, 1H), 5.05-4.91 (m, 2H), 3.5 (d, J=6, 2H).

1.3 2-allyl-1,4-dichloro-3-(methoxymethoxy)benzene

Dry sodium hydride (15 g, 60% in mineral oil, 369 mmol) was suspended in tetrahydrofuran (250 mL) and cooled to 0° C. under N$_2$. 2-allyl-3,6-dichloro-phenol (50 g, 246 mmol) was dissolved in tetrahydrofuran (250 mL) and added dropwise to the sodium hydride suspension over 30 min. The reaction mixture was then allowed to stir at room temperature for a further 2 h. Chloromethyl methyl ether (56 ml, 59 g, 739 mmol) was then added over 30 min and the reaction stirred a further 2 h.

The reaction mixture was concentrated in vacuo and the residue partitioned between ethyl acetate and 0.1M NaOH. The aqueous layer was extracted with ethyl acetate (×2). The organic layers were combined, washed with 0.1M NaOH, then with brine, dried over Na$_2$SO$_4$, and concentrated under reduced pressure to afford 2-allyl-1,4-dichloro-3-(methoxymethoxy)benzene (55 g, 90%).

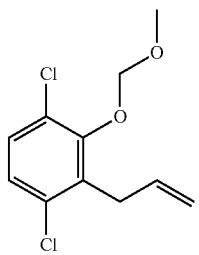

¹H NMR (400 MHz, CDCl₃): δ: 7.20 (d, J=8.6, 1H), 7.11 (d, J=8.6, 1H), 5.99-5.89 (m, 1H), 5.09-4.99 (m, 4H), 3.63 (s, 5H).

1.4 2-[3,6-dichloro-2-(methoxymethoxy)phenyl] acetic Acid

In a 10 L reaction flask, a mixture of 2-allyl-1,4-dichloro-3-(methoxymethoxy)benzene (55 g, 223 mmol), dichloromethane (680 ml), acetonitrile (680 ml) and water (1000 ml) was cooled to 0° C. using an ice-salt bath. Ruthenium (III) chloride (8.7 g, 33.4 mmol) was added to the stirred biphasic mixture. Sodium periodate (338 g, 1.11 mol) was slowly added in small lots maintaining the temperature of the reaction mass below 5° C. (an exotherm of 10-12° C. was observed). The reaction mass was allowed to warm to RT and stirred for an additional 4 h. The mixture was filtered through celite and then phase separated. The aqueous layer was extracted with additional dichloromethane (3×1000 ml). The combined organics were washed with saturated sodium metabisulfite solution (3×500 ml) then brine (500 ml). Evaporation in vacuo afforded 2-[3,6-dichloro-2-(methoxymethoxy)phenyl]acetic acid (50 g, 84%) in acceptable purity.

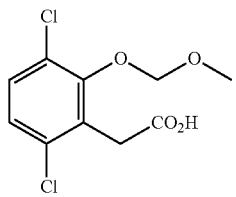 [SMILES: COCOc1c(Cl)ccc(Cl)c1CC(=O)O]

¹H NMR (400 MHz, CDCl₃): δ: 7.28 (d, J=8.6, 1H), 7.14 (d, J=8.6, 1H), 5.10 (s, 2H), 3.97 (s, 2H), 3.59 (s, 3H).

1.5 methyl 2-(3,6-dichloro-2-hydroxy-phenyl)acetate

2-[3,6-dichloro-2-(methoxymethoxy)phenyl]acetic acid (50 g, 189 mmol) in methanol (450 mL) was stirred at 0-5° C. Conc. sulphuric acid (4 mL) was added slowly to the methanolic solution over a period of 20 min. The reaction mass was then slowly heated to reflux over a period of 3 h. The reaction was monitored by TLC and when judged complete, methanol was distilled out under reduced pressure and the residue poured into saturated aqueous NaHCO₃ solution. The aqueous was extracted with ethyl acetate and the combined organics washed with brine. The organics were concentrated to afford crude product. The crude was purified by trituration with ethyl acetate-hexane to obtain methyl 2-(3,6-dichloro-2-hydroxy-phenyl)acetate (32 g, 72%) as an off-white solid.

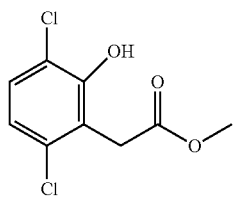

¹H NMR (400 MHz, CDCl₃): δ: 7.19 (d, J=8.7, 1H), 6.94 (d, J=8.6, 1H), 6.14 (bs, 1H), 3.89 (s, 2H), 3.72 (s, 3H).

1.6 methyl 2-[3,6-dichloro-2-[(2-chlorothiazol-5-yl)methoxy]phenyl]acetate

To a stirred solution of methyl 2-(3,6-dichloro-2-hydroxyphenyl)acetate (15 g, 63.8 mmol) in acetone (450 mL) was added potassium carbonate (13.2 g, 95.7 mmol). 2-Chloro-5-chloromethylthiazole (11.8 g, 70.2 mmol) in acetone (450 mL) was added dropwise. After completion of the addition the reaction was stirred at RT for 6 h. Solids were removed by filtration and the filtrate evaporated under reduced pressure to give crude product. Purification by flash column chromatography gave methyl 2-[3,6-dichloro-2-[(2-chlorothiazol-5-yl)methoxy]phenyl]acetate (14.5 g, 62%).

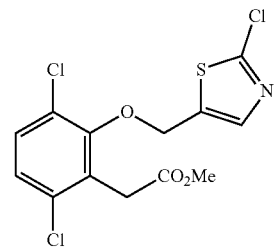 [SMILES: COC(=O)Cc1c(Cl)ccc(Cl)c1OCc1cnc(Cl)s1]

¹H NMR (400 MHz, CDCl₃): δ: 7.51 (s, 1H), 7.30 (d, J=8.6, 1H), 7.17 (d, J=8.7, 1H), 3.83 (s, 2H), 3.72 (s, 3H).

1.7 2-[3,6-dichloro-2-[(2-chlorothiazol-5-yl)methoxy]phenyl]acetic Acid

To a stirred solution of methyl 2-[3,6-dichloro-2-[(2-chlorothiazol-5-yl)methoxy]phenyl]acetate (14.5 g, 39.6 mmol) in tetrahydrofuran (75 mL) and water (75 mL) was added lithium hydroxide monohydrate. The reaction mixture was stirred at RT for 16 h. The organics were evaporated under reduced pressure and the aqueous residue acidified with 2N HCl. The mixture was extracted with ethyl acetate (×3), the combined organics washed with brine, dried over Na₂SO₄, filtered and evaporated to obtain 2-[3,6-dichloro-2-[(2-chlorothiazol-5-yl)methoxy]phenyl]acetic acid (12 g, 86%).

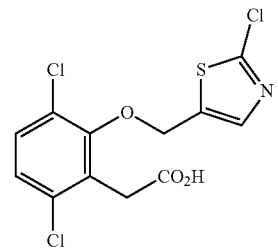 [SMILES: O=C(O)Cc1c(Cl)ccc(Cl)c1OCc1cnc(Cl)s1]

¹H NMR (400 MHz, DMSO-d6): δ: 12.67 (bs, 1H), 7.78 (s, 1H), 7.52 (d, J=8.7, 1H), 7.36 (d, J=8.6, 1H), 5.20 (s, 2H), 3.75 (s, 2H).

1.8 methyl 4-[[2-[3,6-dichloro-2-[(2-chlorothiazol-5-yl)methoxy]phenyl]acetyl]amino]thiazole-5-carboxylate To a stirred solution of 2-[3,6-dichloro-2-[(2-chlorothiazol-5-yl)methoxy]phenyl]acetic acid (1.00 g, 2.84 mmol, 1 eq.) in dichloromethane (10 mL) was added N,N-dimethylformamide (0.05 mL) and the mixture cooled in an ice-water bath. Oxalyl chloride (0.5 mL, 5.96 mmol, 2.1 eq.) was added dropwise and reaction stirred at RT for 1 h.

The mixture was evaporated to dryness and re-dissolved in dichloromethane (10 mL). Separately, methyl 4-amino-5-thiazolecarboxylate (381 mg, 2.41 mmol, 0.85 eq.) was dissolved in dichloromethane (10 mL) and pyridine (0.6 mL, 8.52 mmol, 3 eq.) and cooled to 0° C. with stirring. The acid chloride solution was added dropwise to the amine at 0° C. After completion of the addition, the reaction mixture was stirred at RT for 2 h.

The mixture was diluted with dichloromethane, washed with 1N HCl, then saturated NaHCO₃ solution, then water and finally brine. The organics were dried over Na₂SO₄, filtered and evaporated to dryness to give a crude residue. Purification by flash column chromatography gave crude product which was further purified by trituration with 20% ether in hexane to obtain methyl 4-[[2-[3,6-dichloro-2-[(2-chlorothiazol-5-yl)methoxy]phenyl]acetyl]amino]thiazole-5-carboxylate (700 mg, 58%) as an off-white solid.

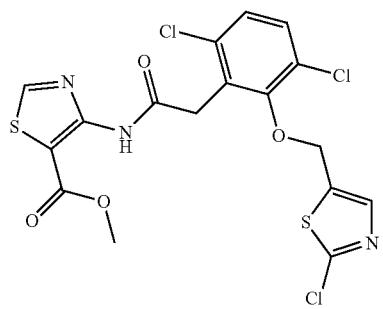 [SMILES: COC(=O)c1scnc1NC(=O)Cc1c(Cl)ccc(Cl)c1OCc1cnc(Cl)s1]

¹H NMR (400 MHz, CDCl₃): δ: 9.99 (br. s, 1H), 8.83 (s, 1H), 7.51 (s, 1H), 7.33 (d, J=8.7, 1H), 7.20 (d, J=8.7, 1H), 5.26 (s, 2H), 4.16 (s, 2H), 3.90 (s, 3H).

1.9 methyl 4-[[2-[3,6-dichloro-2-[(2-chlorothiazol-5-yl)methoxy]phenyl]acetyl]-prop-2-ynyl-amino]thiazole-5-carboxylate To a stirred solution of methyl 4-[[2-[3,6-dichloro-2-[(2-chlorothiazol-5-yl)methoxy]phenyl]acetyl]amino]thiazole-5-carboxylate (700 mg, 1.42 mmol, 1 eq.) in acetonitrile (10 mL) was added potassium carbonate (294 mg, 2.13 mmol, 1.5 eq.) and propargyl bromide (0.2 mL, 2.13 mmol, 1.5 eq.) at RT. The reaction mixture was then refluxed for 14 h.

The reaction was cooled to RT, diluted with water and ethyl acetate, and phase separated. The aqueous layer was re-extracted with further ethyl acetate. The combined organics were washed with brine, dried over Na₂SO₄, filtered and evaporated to obtain a crude residue. Purification by flash column chromatography gave methyl 4-[[2-[3,6-dichloro-2-[(2-chlorothiazol-5-yl)methoxy]phenyl]acetyl]-prop-2-ynyl-amino]thiazole-5-carboxylate (300 mg, 40%) as a yellow oil.

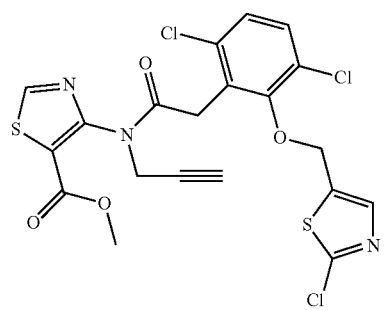 [SMILES: C#CCN(C(=O)Cc1c(Cl)ccc(Cl)c1OCc1cnc(Cl)s1)c1ncsc1C(=O)OC]

¹H NMR (400 MHz, CDCl₃): δ: 8.89 (s, 1H), 7.68 (s, 1H), 7.25 (m, 1H), 7.12 (d, J=8.4, 1H), 5.15 (s, 2H), 4.65 (s, 2H), 3.88 (s, 3H), 3.69 (s, 2H), 2.15 (s, 1H).

1.10 6-[3,6-dichloro-2-[(2-chlorothiazol-5-yl)methoxy]phenyl]-7-hydroxy-4-prop-2-ynyl-thiazolo[4,5-b]pyridin-5-one To a stirred solution of methyl 4-[[2-[3,6-dichloro-2-[(2-chlorothiazol-5-yl)methoxy]phenyl]acetyl]-prop-2-ynyl-amino]thiazole-5-carboxylate (300 mg, 0.565 mmol, 1.0 eq.) in N,N-dimethylformamide (2 mL) was added sodium hydride (34 mg, 60% dispersed in oil, 0.848 mmol, 1.5 eq.) at 0° C. The reaction mixture was then allowed to warm to ambient temperature and stirred at RT for 1 h. The reaction was quenched with 2N HCl and extracted with ethyl acetate. The organic layer was evaporated to give a crude residue which was purified by flash column chromatography to obtain 6-[3,6-dichloro-2-[(2-chlorothiazol-5-yl)methoxy]phenyl]-7-hydroxy-4-prop-2-ynyl-thiazolo[4,5-b]pyridin-5-one (213 mg, 75%) as an off-white solid.

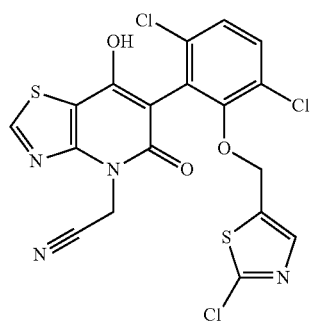 [SMILES: N#CCn1c(=O)c(-c2c(Cl)ccc(Cl)c2OCc2cnc(Cl)s2)c(O)c2scnc21]

¹H NMR (400 MHz, DMSO-d6): δ: 11.57 (bs, 1H), 9.46 (s, 1H), 7.59 (d, J=8.7, 1H), 7.48 (s, 1H), 7.42 (d, J=8.7, 1H), 5.09-4.99 (m, 4H), 3.13 (s, 1H).

Example 2 Preparation of 6-(2-benzyloxy-3,6-dichloro-phenyl)-7-hydroxy-4-prop-2-ynyl-[1,2,5]thiadiazolo[3,4-b]pyridin-5-one

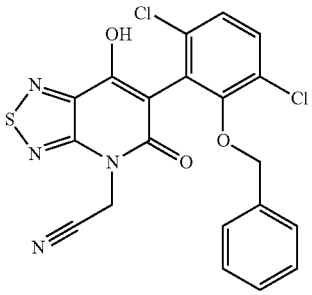 [SMILES: N#CCn1c(=O)c(-c2c(Cl)ccc(Cl)c2OCc2ccccc2)c(O)c2nsnc21]

2.1 2-Allyl-3,6-dichloro-phenol

A mixture of 2-allyloxy-1,4-dichloro-benzene (1.0 g, 4.9 mmol) and N,N-dimethylformamide (0.1 mL) was heated at an external temperature of 220° C. for 1 hour. The mixture was allowed to cool to room temperature and was concentrated in vacuo to provide 2-allyl-3,6-dichloro-phenol as a brown oil (0.99 g, 99%).

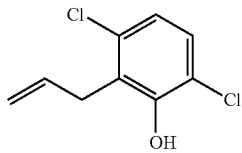

$^1$H NMR (400 MHz, CDCl$_3$): δH: 7.18-7.08 (m, 1H), 6.95-6.85 (m, 1H), 6.02-5.84 (m, 1H), 5.71 (s, 1H), 5.14-4.99 (m, 2H), 3.59 (dt, 2H).

2.2 2-Allyl-3-benzyloxy-1,4-dichloro-benzene

Benzyl bromide (3.2 mL, 27 mmol) was added to a suspension of 2-allyl-3,6-dichloro-phenol (5.0 g, 25 mmol) and potassium carbonate (3.7 g, 27 mmol) in acetone (49 mL) and the mixture was heated at reflux for 6 h. The mixture was allowed to cool to room temperature and was filtered. The filtrate was concentrated in vacuo and the crude product was purified by flash column chromatography to provide 2-allyl-3-benzyloxy-1,4-dichloro-benzene (4.03 g, 56%) as a colourless oil.

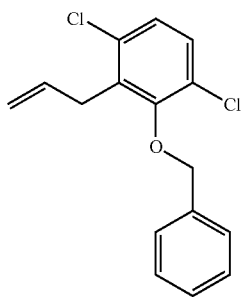 [SMILES: C=CCc1c(Cl)ccc(Cl)c1OCc1ccccc1]

$^1$H NMR (400 MHz, CDCl$_3$): δ$_H$: 7.54-7.49 (2H, m), 7.45-7.35 (4H, m), 7.27-7.24 (1H, m), 7.15 (1H, d), 6.01-5.90 (1H, m), 5.10-4.97 (4H, m), 3.59 (2H, dt).

2.3 2-(2-Benzyloxy-3,6-dichloro-phenyl)acetic Acid

Ruthenium(III) chloride (0.212 g, 1.02 mmol) was added to a solution of 2-allyl-3-benzyloxy-1,4-dichloro-benzene (15.0 g, 51.1 mmol) in a mixture of water (153 mL), acetonitrile (102 mL) and ethyl acetate (102 mL). Sodium periodate (54.8 g, 255 mmol) was added portionwise over a period of 1 hour keeping the internal temperature below 25° C. The reaction was stirred for 3 hours then cooled to 5° C. The reaction mixture was quenched by the addition of an solution of sodium metabisulfite (97.2 g, 511 mmol) in water (500 mL). The mixture was extracted with dichloromethane (2×500 mL). The combined organic extracts were dried over MgSO$_4$, filtered and concentrated in vacuo. The residue was partitioned between a saturated aqueous solution of NaHCO$_3$ (200 mL) and dichloromethane (200 mL). The aqueous layer was kept and acidified to pH 1 by addition of concentrated hydrochloric acid (20 mL). The mixture was extracted with dichloromethane (3×100 mL) and the combined organic extracts were dried over MgSO$_4$, filtered and concentrated in vacuo. The crude product was recrystallized from diethyl ether to provide 2-(2-benzyloxy-3,6-dichloro-phenyl)acetic acid (2.51 g, 16%) as a white solid.

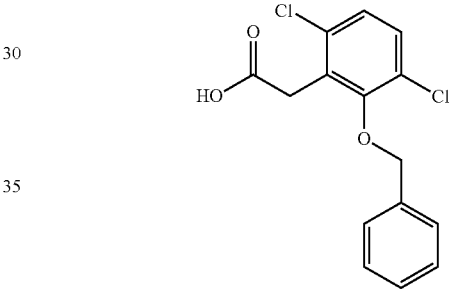

$^1$H NMR (400 MHz, CDCl$_3$): δ$_H$: 7.48-7.44 (2H, m), 7.42-7.31 (4H, m), 7.17 (1H, d), 5.04 (2H, s), 3.85 (2H, s).

2.4 methyl 4-amino-1,2,5-thiadiazole-3-carboxylate 4-amino-1,2,5-thiadiazole-3-carboxylic acid (500 mg, 3.44 mmol, 1.0 eq.) was suspended in ethyl acetate (10 mL) and tetrahydrofuran (3 mL) with stirring under N$_2$. Treated with solid 1,1'-carbonyldiimidazole (670 mg, 4.13 mmol, 1.2 eq.).

After 2 h, the reaction was quenched with methanol (18 ml). Further methanol was then added until all material dissolved (to a total reaction volume of ~50 ml). The reaction was evaporated to dryness to afford a crude yellow solid. The crude was partitioned between ethyl acetate and sat. NaHCO$_3$ (aq). The organic layer was kept and the aqueous re-extracted. The combined organics were dried over Na$_2$SO$_4$, filtered and evaporated to give methyl 4-amino-1,2,5-thiadiazole-3-carboxylate (338 mg, 61.6%), as a yellow solid.

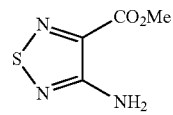

$^1$H NMR (400 MHz, CDCl$_3$): δ$_H$: 5.95 (br. s, 2H), 4.00 (s, 3H).

2.5 methyl 4-[[2-(2-benzyloxy-3,6-dichloro-phenyl) acetyl]amino]-1,2,5-thiadiazole-3-carboxylate 2-(2-benzyloxy-3,6-dichloro-phenyl)acetic acid (300 mg, 0.964 mmol, 1.0 eq.) was suspended in dichloromethane (3 ml) under N$_2$ and a drop of N,N-dimethylformamide added. The mixture was treated with oxalyl chloride (0.17 mL, 1.93 mmol, 2.0 eq.) and immediately started to effervesce. Stirred at rt for 2.5 h.

The reaction mixture was evaporated to dryness and the crude acyl chloride redissolved in dichloromethane (2.5 ml). With stirring, solid methyl 4-amino-1,2,5-thiadiazole-3-carboxylate (153 mg, 0.96 mmol, 1.0 eq.) was added, followed by pyridine (0.16 mL, 1.93 mmol, 2.0 eq.). The reaction was stirred at rt for 1 h then diluted with further dichloromethane and quenched with sat. NaHCO$_3$ (aq). The mixture was phase-separated and the organics dried over Na$_2$SO$_4$. Evaporation to dryness gave a crude solid which was further purified by flash column chromatography (silica, eluent 0-80% ethyl acetate in isohexane). The target methyl 4-[[2-(2-benzyloxy-3,6-dichloro-phenyl)acetyl]amino]-1,2,5-thiadiazole-3-carboxylate was obtained as a white solid (251 mg, 57.6%).

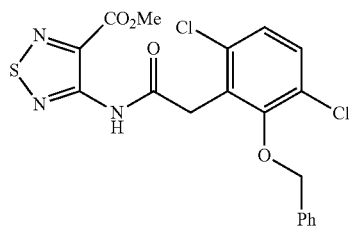 [SMILES: COC(=O)c1nsnc1NC(=O)Cc1c(Cl)ccc(Cl)c1OCc1ccccc1]

$^1$H NMR (400 MHz, d6-DMSO): δ$_H$: 11.46 (br. s, 1H), 7.56-7.29 (m, 7H), 4.96 (s, 2H), 4.01 (s, 2H), 3.72 (s, 3H).

2.6 6-(2-benzyloxy-3,6-dichloro-phenyl)-7-hydroxy-4-prop-2-ynyl-[1,2,5]thiadiazolo[3,4-b]pyridin-5-one Sodium hydride (25 mg, 60% wt in mineral oil, 0.64 mmol, 1.2 eq.) was suspended in tetrahydrofuran (1 mL) under N$_2$. A solution was prepared of methyl 4-[[2-(2-benzyloxy-3,6-dichloro-phenyl)acetyl]amino]-1,2,5-thiadiazole-3-carboxylate (240 mg, 0.53 mmol, 1.0 eq.) in tetrahydrofuran (2 mL) and N,N-dimethylformamide (2 mL). This solution was added dropwise to the stirred NaH. A strong orange colour rapidly formed. After 5 min, propargyl bromide (0.065 mL, 0.58 mmol, 1.1 eq.) was added. The reaction was stirred at rt.

After a total reaction time of 1 h 20 min, a second charge of sodium hydride (8 mg) was added. After a further 40 min, the reaction was quenched with sat. NH$_4$Cl (aq). Brine was added, and the mixture extracted into ethyl acetate. The organics were dried over Na$_2$SO$_4$ and solvent removed in vacuo to give a crude residue. Purification by preparative HPLC purification gave product 6-(2-benzyloxy-3,6-dichloro-phenyl)-7-hydroxy-4-prop-2-ynyl-[1,2,5]thiadiazolo[3,4-b]pyridin-5-one (40 mg, 16%) as a yellow solid.

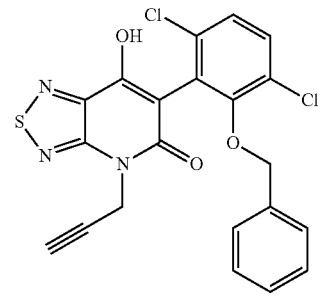 [SMILES: C#CCn1c(=O)c(-c2c(Cl)ccc(Cl)c2OCc2ccccc2)c(O)c2nsnc21]

$^1$H NMR (400 MHz, CDCl$_3$): δ$_H$: 7.44 (d, J=8.7 Hz, 1H), 7.26 (d, J=8.7 Hz, 1H), 7.17-7.10 (m, 2H), 7.07-6.99 (m, 3H), 5.04-4.89 (m, 4H), 2.24 (t, J=2.5 Hz, 1H).

Compounds 1.19, 3.19, 5.22, 9.22, 13.22 and 15.22 were prepared using the general methods as described supra. Table 18 below shows the structure of these compounds and NMR characterising data.

TABLE 18

Preparation examples of compounds of forumula (I), wherein A$_2$ is NR$^{11}$, G is H, T is Tp, X$^{22}$ is H, X$^{23}$ is H, and X$^{24}$ is Cl, and A$_3$, A$_4$, A$_5$, R$^{11}$, X$^{21}$ and D are as shown in the table.

| Compound | A$_3$ | A$_4$ | A$_5$ | R$^{11}$ | X$^{21}$ | D | NMR details |
|---|---|---|---|---|---|---|---|
| 1.19 | C(O) | S | CH | —CH$_2$C≡CH | Cl | 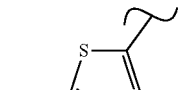 | $^1$H NMR (400 MHz, d6-DMSO): δ$_H$: 11.57 (br. s, 1H), 9.46 (s, 1H), 7.59 (d, J = 8.7 1H), 7.48 (s, 1H), 7.42 (d, J = 8.7, 1H), 5.09-4.99 (m, 4H), 3.13 (s, 1H). |
| 3.19 | C(O) | S | CH | —CH$_2$CHF$_2$ | Cl | 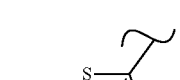 | $^1$H NMR (400 MHz, d6-DMSO): δ$_H$: 11.67 (br. s, 1H), 9.44 (s, 1H), 7.59 (d, J = 8.7, 1H), 7.47 (s, 1H), 7.42 (d, J = 8.6, 1H), 6.45-6.17 (m, 1H), 5.03 (s, 2H), 4.76-4.69 (m, 2H). |
| 5.22 | S(O)$_2$ | S | CH | —CH$_2$C≡CH | Cl | Phenyl- | $^1$H NMR (400 MHz, d6-DMSO): δ$_H$: 9.38-9.29 (m, 1H), 7.67 (d, J = 8.7 Hz, 1H), 7.45 (d, J = 8.8 Hz, 1H), 7.35-7.21 (m, 6H), 6.63 (t, J = 5.9 Hz, 1H), 5.37 (dd, J = 6.2, 11.9 Hz, 1H), 5.26 |

TABLE 18-continued

Preparation examples of compounds of forumula (I), wherein $A_2$ is $NR^{11}$, G is H, T is Tp, $X^{22}$ is H, $X^{23}$ is H, and $X^{24}$ is Cl, and $A_3$, $A_4$, $A_5$, $R^{11}$, $X^{21}$ and D are as shown in the table.

| Compound | $A_3$ | $A_4$ | $A_5$ | $R^{11}$ | $X^{21}$ | D | NMR details |
|---|---|---|---|---|---|---|---|
| 9.22 | C(O) | N | S | —CH$_2$C≡CH | Cl | Phenyl- | (dd, J = 6.2, 11.8 Hz, 1H), 5.00-4.94 (m, 1H), 4.91-4.82 (m, 1H). $^1$H NMR (400 MHz, CDCl$_3$): $\delta_H$: 7.44 (d, J = 8.7 Hz, 1H), 7.26 (d, J = 8.7 Hz, 1H), 7.17-7.10 (m, 2H), 7.07-6.99 (m, 2H), 5.04-4.89 (m, 4H, 2.24 (t, J = 2.5 Hz, 1H). |
| 13.22 | S(O)$_2$ | S | CH | —CH$_2$CHF$_2$ | Cl | Phenyl- | $^1$H NMR (400 MHz, d6-DMSO): $\delta_H$: 9.38 (s, 1H), 7.71-7.65 (m, J = 8.8 Hz, 1H), 7.54-7.39 (m, J = 8.8 Hz, 1H), 7.29-7.22 (m, 5H), 6.23 (tt, J = 3.9, 55.5 Hz, 1H), 4.96-4.86 (m, 1H), 4.32-4.01 (m, 2H) |
| 15.22 | C(O) | CH | S | —CH$_2$C≡CH | F | Phenyl- | $^1$H NMR (400 MHz, d6-DMSO): $\delta_H$: 11.99 (br. s, 1H), 8.87 (s, 1H), 7.64-7.56 (m, 1H), 7.22-7.05 (m, 6H), 4.95 (d, 1H), 4.87-4.76 (m, 3H), 3.32 (m, 1H). |

BIOLOGICAL EXAMPLES

B1 Post-Emergence Efficacy

Seeds of a variety of test species are sown in standard soil in pots: —*Solanum nigrum* (SOLNI), *Amaranthus retoflexus* (AMARE), *Setaria faberi* (SETFA), *Echinochloa crus-galli* (ECHCG), *Ipomoea hederacea* (IPOHE), *Lolium perenne* (LOLPE). After 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds are applied at 1000 g/ha and 250 g/ha. The test plants are then grown in a glasshouse under controlled conditions in a glasshouse (at 24/16° C., day/night; 14 hours light; 65% humidity) and watered twice daily. After 13 days, the test is evaluated for the percentage damage caused to the plant. The biological activities are assessed on a five point scale (5=80-100%; 4=60-79%; 3=40-59%; 2=20-39%; 1=0-19%). A blank value in the table is indicative that the compound was not tested on that species.

TABLE 19

Control of weed species by compounds of formula (I) after post-emergence application

| Compound | Application rate (g/ha) | AMARE | SOLNI | SETFA | LOLPE | ECHCG | IPOHE |
|---|---|---|---|---|---|---|---|
| 1.19 | 1000 | 5 | 5 | 5 | 5 | 5 | 5 |
|  | 250 | 5 | 5 | 5 | 5 | 5 | 5 |
| 3.19 | 1000 | 5 | 5 | 5 | 5 | 5 | 5 |
|  | 250 | 5 | 5 | 5 | 5 | 4 | 5 |
| 5.22 | 1000 | 1 | 1 | 2 | 2 | 2 | 2 |
|  | 250 | 2 | 1 | 1 | 2 | 2 | 2 |
| 9.22 | 1000 | 5 | 5 | 5 | 5 | 3 | 5 |
|  | 250 | 4 | 4 | 2 | 4 | 2 | 5 |
| 13.22 | 1000 | 2 | 4 | 2 | 2 | 2 | 5 |
|  | 250 | 3 | 3 | 1 | 2 | 1 | 4 |

TABLE 19-continued

Control of weed species by compounds of formula
(I) after post-emergence application

| Compound | Application rate (g/ha) | AMARE | SOLNI | SETFA | LOLPE | ECHCG | IPOHE |
|---|---|---|---|---|---|---|---|
| 15.22 | 1000 | 5 | 5 | 3 | 4 | 3 | 3 |
|  | 250 | 4 | 4 | 1 | 3 | 2 | 4 |

The invention claimed is:

1. A compound of formula (I),

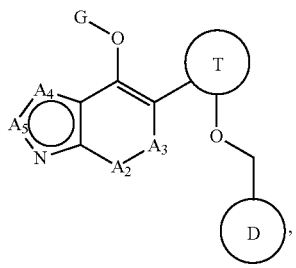

or a salt or N-oxide thereof, wherein, $A_2$ is $CR^{10a}R^{10b}$ or $NR^{11}$;

$A_3$ is $C(O)$ or $S(O)_2$;

$A_4$ is $CR^1$, $N(R^{13})_n$, O or S;

$A_5$ is $CR^2$, $N(R^{14})_n$, O or S;

n is an integer of 0 or 1;

$R^1$ is independently hydrogen, halogen, nitro, cyano, or independently selected from the group consisting of: $C_1$-$C_6$alkyl, $C_2$-$C_6$ alkenyl, $C_1$-$C_6$ alkoxy $C_1$-$C_6$ alkylthio, $C_1$-$C_6$alkylsulfinyl, $C_1$-$C_6$alkylsulfonyl, $C_3$-$C_6$cycloalkyl, $C_1$-$C_6$ alkoxy-$C_1$-$C_6$alkyl-, $C_1$-$C_6$alkoxy-$C_1$-$C_6$alkoxy-, di-$C_1$-$C_6$alkoxy-$C_1$-$C_6$alkyl, and $C_1$-$C_6$alkylthio-$C_1$-$C_6$alkyl, each of which is optionally substituted by 1-3 halogen atoms;

$R^2$ is hydrogen, halogen, methyl or $C_1$haloalkyl;

$R^{10a}$ and $R^{10b}$ are each independently hydrogen, halogen, cyano, $C_1$-$C_8$alkyl, $C_1$-$C_8$alkoxy-$C_1$-$C_4$alkyl-, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkyl-, heterocyclyl, heterocyclyl-$C_1$-$C_4$alkyl-, or $C_1$-$C_8$alkoxycarbonyl-; or $R^{10a}$ and $R^{10b}$ together with the carbon atom they are attached to join to form a 3- to 10-membered carbocyclic ring or a 4- to 10-membered heterocyclic ring;

$R^{11}$ is hydrogen, $C_1$-$C_{10}$alkyl, $C_1$-$C_4$haloalkyl, $C_2$-$C_{10}$alkenyl, $C_2$-$C_4$haloalkenyl, $C_2$-$C_{10}$alkynyl, $C_2$-$C_4$haloalkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^{12}$, or heterocyclyl-$C_1$-$C_6$alkyl- or heterocyclyl-$C_1$-$C_6$alkyl- wherein the heterocyclyl moiety is substituted by one to three $R^{12}$;

each $R^{12}$ is independently halogen, $C_1$-$C_4$alkyl, $C_1$-$C_4$haloalkyl, $C_1$-$C_4$alkoxy or $C_1$-$C_4$haloalkoxy;

$R^{13}$ is hydrogen, $C_1$-$C_3$alkyl, or $C_1$-$C_3$haloalkyl;

$R^{14}$ is hydrogen, methyl or $C_1$haloalkyl;

G is hydrogen, or $C(O)R^3$;

$R^3$ is selected from the group consisting of $C_1$-$C_6$alkyl, $C_1$-$C_6$alkenyl, $C_1$-$C_6$alkynyl, $C_1$-$C_6$alkoxy, $C_1$-$C_6$alkyl-S—, —$NR^4R^5$ and phenyl optionally substituted by one or more $R^6$;

$R^4$ and $R^5$ are independently selected from the group consisting of $C_1$-$C_6$ alkyl and $C_1$-$C_6$ alkoxy, or $R^4$ and $R^5$ together can form a morpholinyl ring;

$R^6$ is selected from the group consisting of halogen, cyano, nitro, $C_1$-$C_3$alkyl, $C_1$-$C_3$haloalkyl, $C_1$-$C_3$alkoxy and $C_1$-$C_3$haloalkoxy; and T is a 5- or 6-membered monocyclic heteroaryl ring system containing 1, 2, or 3 heteroatoms independently selected from nitrogen, oxygen and sulphur, said 5-membered ring system being substituted by one or more radicals selected from X, Y, and $R^7$, and said 6-membered ring system being substituted by one or more radicals selected from $X^1$, $X^2$, $X^3$, $X^4$ and $R^7$, and wherein the oxy-alkyl-D moiety and the bi-cyclic moiety are linked via ring T such that they are situated ortho with respect to each other;

or T is a substituted phenyl ring of formula (Tp)

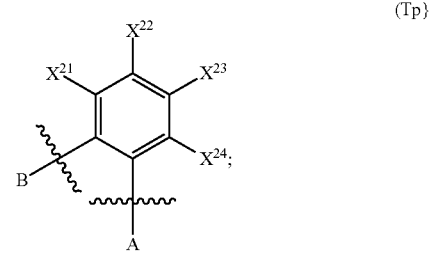

each X, $X^3$, $X^{23}$ and each Y are independently hydrogen, $C_1$-$C_3$ alkyl, $C_1$-$C_3$ alkoxy, $C_1$-$C_3$haloalkyl, $C_1$-$C_3$haloalkoxy, or halogen;

$X^1$ is oxo, $C_1$-$C_3$ alkyl, $C_1$-$C_3$ alkoxy, $C_1$-$C_3$haloalkyl, $C_1$-$C_3$haloalkoxy, or halogen;

$X^2$, and $X^4$ are independently hydrogen, $C_1$-$C_3$ alkyl, $C_1$-$C_3$ alkoxy, $C_1$-$C_3$haloalkyl, $C_1$-$C_3$haloalkoxy, oxo, or halogen;

$X^{21}$ is $C_1$-$C_3$ alkyl, $C_1$-$C_3$ alkoxy, $C_1$-$C_3$haloalkyl, $C_1$-$C_3$haloalkoxy, or halogen;

$X^{22}$, and $X^{24}$ are independently hydrogen, $C_1$-$C_3$ alkyl, $C_1$-$C_3$ alkoxy, $C_1$-$C_3$haloalkyl, $C_1$-$C_3$haloalkoxy, or halogen;

$R^7$ is hydrogen, $C_1$-$C_3$ alkyl, $C_1$-$C_3$ alkoxy, $C_1$-$C_3$haloalkyl, $C_1$-$C_3$haloalkoxy;

A denotes the point of attachment to the oxy-alkyl-D moiety and B denotes the point of attachment to the bi-cyclic moiety; and D is a substituted or unsubstituted monocyclic heteroaryl ring containing 1, 2, or 3 heteroatoms independently selected from oxygen, nitrogen and sulphur, and wherein when D is substituted it is substituted on at least one ring carbon atom with $R^8$ and/or on a ring nitrogen atom with $R^9$;

or D is the group (Dp)

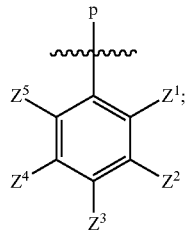

(Dp)

each $R^8$ is independently oxygen, hydroxyl, halogen, cyano, $C_1$-$C_6$alkyl, $C_1$-$C_6$haloalkyl, $C_1$-$C_6$haloalkoxy, $C_1$-$C_3$haloalkoxy-$C_1$-$C_3$alkyl-, $C_1$-$C_6$alkoxy, $C_1$-$C_3$alkoxy-$C_1$-$C_3$alkyl, $C_1$-$C_3$alkoxy-$C_1$-$C_3$alkoxy-$C_1$-$C_3$alkyl-, $C_3$-$C_6$cycloalkyl, $C_2$-$C_6$ alkenyl, $C_2$-$C_6$ haloalkenyl, $C_2$-$C_6$ alkynyl, $C_1$-$C_6$hydroxyalkyl-, $C_1$-$C_6$alkylcarbonyl-, $C_1$-$C_6$alkyl-S(O)$_m$—, amino, $C_1$-$C_6$alkylamino, $C_1$-$C_6$dialkylamino, —C($C_1$-$C_3$alkyl)=N—O—$C_1$-$C_3$alkyl and $C_2$-$C_6$ haloalkynyl;

m is an integer of 0, 1, or 2;

each $R^9$ is independently, $C_1$-$C_4$ alkyl, $C_3$-$C_6$alkoxy, $C_1$-$C_2$ alkoxy-$C_1$-$C_2$ alkyl, $C_2$-$C_4$ alkenyl, $C_1$-$C_4$ haloalkyl, $C_2$-$C_4$ haloalkenyl, $C_2$-$C_4$ alkynyl or $C_2$-$C_4$ haloalkynyl;

p denotes the point of attachment of (Dp) to the rest of the molecule; and $Z^1$, $Z^2$, $Z^3$, $Z^4$, and $Z^5$ are each independently selected from hydrogen, $C_1$-$C_3$ alkyl, $C_1$-$C_3$ alkoxy, $C_1$-$C_3$haloalkyl, $C_1$-$C_3$haloalkoxy, or halogen;

provided that when $A_4$ is S, $A_2$ is $NR^{11}$, and $A^3$ is C(O), then T is not (Tp) when D is (Dp).

2. The compound according to claim 1, wherein G is hydrogen, or C(O)$R^3$ wherein $R^3$ is $C_1$-$C_4$ alkyl, $C_1$-$C_4$alkoxy, $C_2$-$C_3$alkenyl, $C_2$-$C_3$alkynyl or —$C_1$-$C_3$alkoxy.

3. The compound according to claim 1, wherein D is a substituted or unsubstituted furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyridonyl, pyrimidinyl, pyridazinyl, pyrazinyl, 1,2,3-triazinyl, 1,2,4-triazinyl, or 1,3,5-triazinyl ring, wherein when D is substituted it is substituted on at least one ring carbon atom with $R^8$ and/or on a ring nitrogen atom with $R^9$.

4. The compound according to claim 1, wherein D is (Dp).

5. The compound according to claim 1, wherein T is selected from the group consisting of (Tp) and (T1) to (T62):

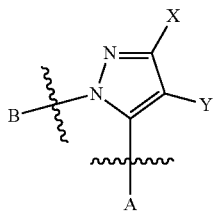

(T1)

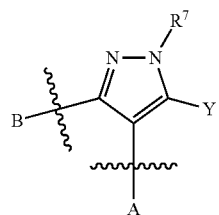

(T2)

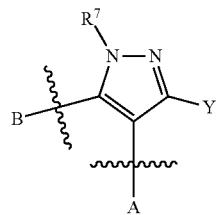

(T3)

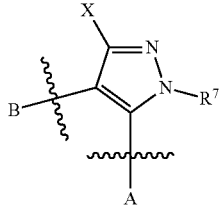

(T4)

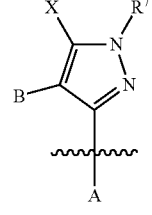

(T5)

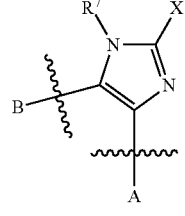

(T6)

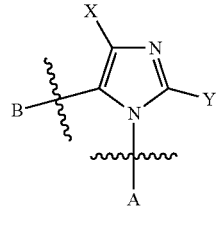

(T7)

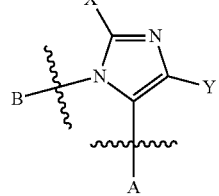

(T8)

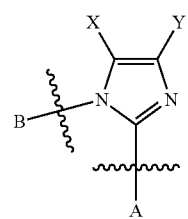 (T9)
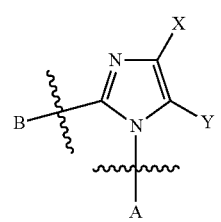 (T10)
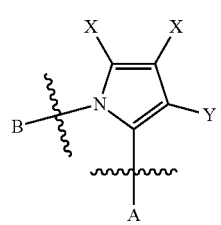 (T11)
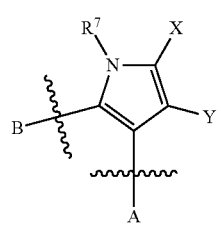 (T12)
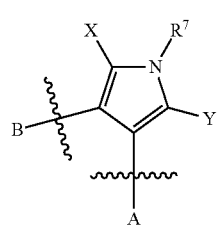 (T13)
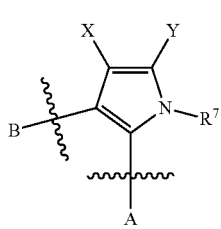 (T14)
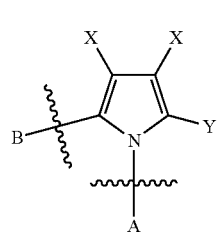 (T15)
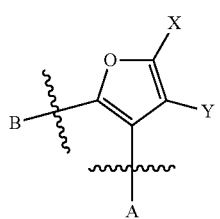 (T16)
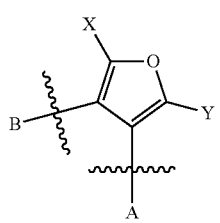 (T17)
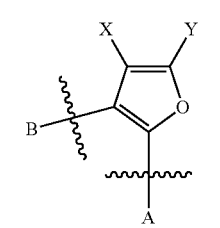 (T18)
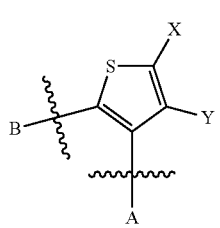 (T19)
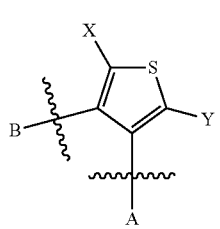 (T20)
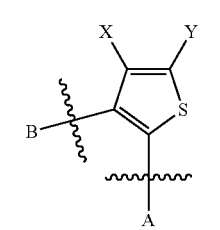 (T21)
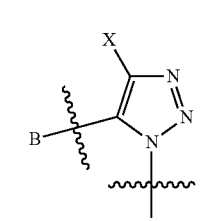 (T22)

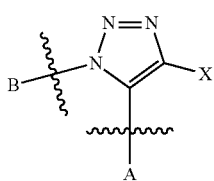 (T23)
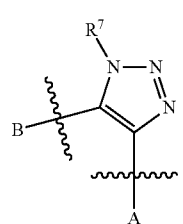 (T24)
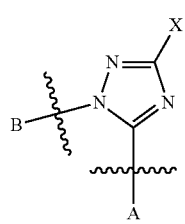 (T25)
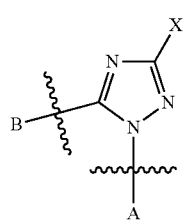 (T26)
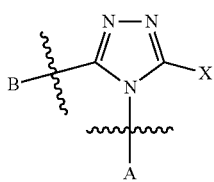 (T27)
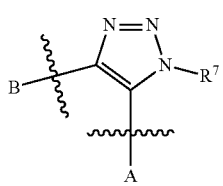 (T28)
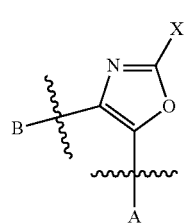 (T29)
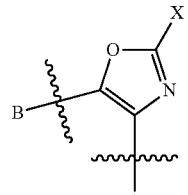 (T30)
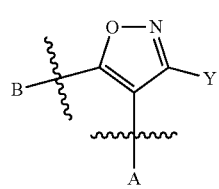 (T31)
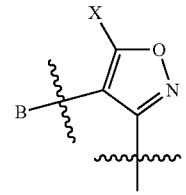 (T32)
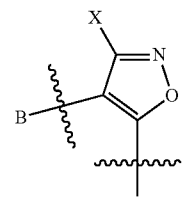 (T33)
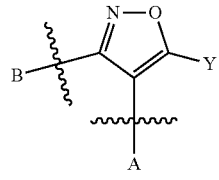 (T34)
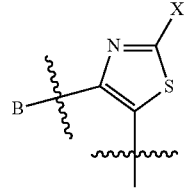 (T35)
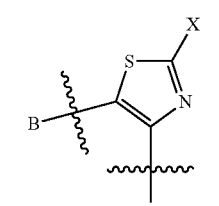 (T36)
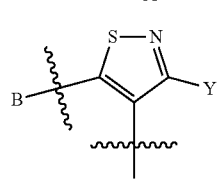 (T37)

(T38) 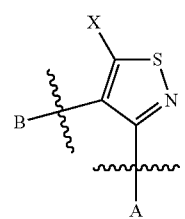
(T39) 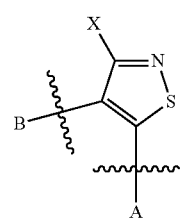
(T40) 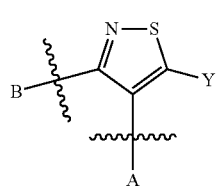
(T41) 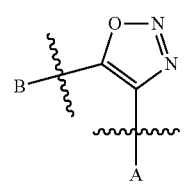
(T42) 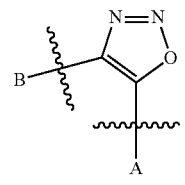
(T43) 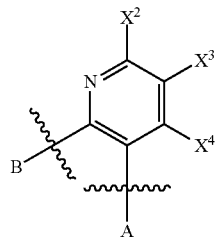
(T44) 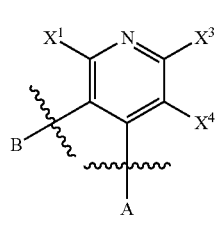
(T45) 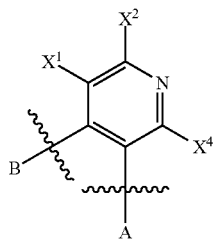
(T46) 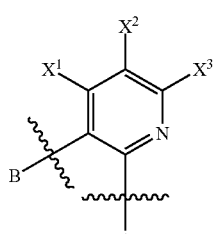
(T47) 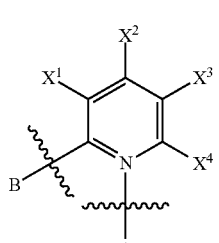
(T48) 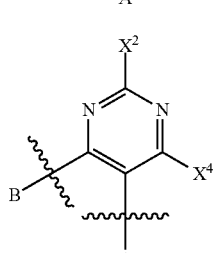
(T49) 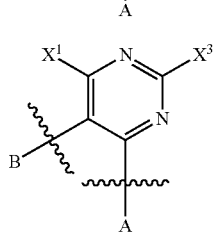
(T50) 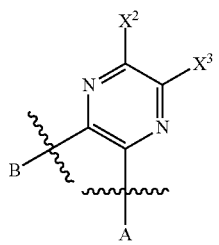
(T51) 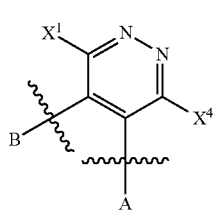

(T52) 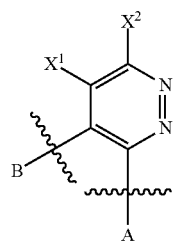
(T53) 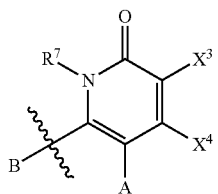
(T54) 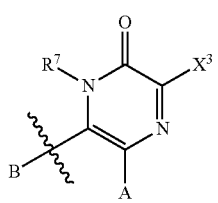
(T55) 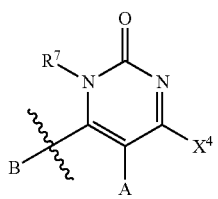
(T56) 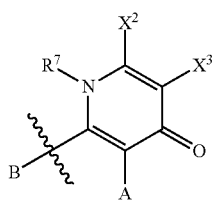
(T57) 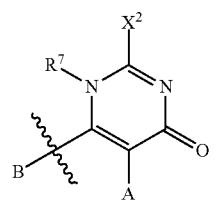
(T58) 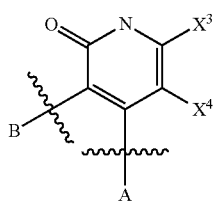
(T59) 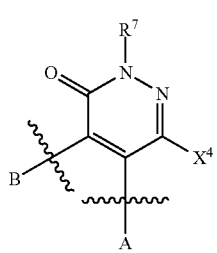
(T60) 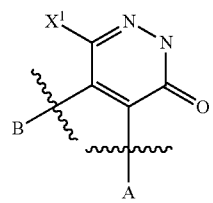
(T61) 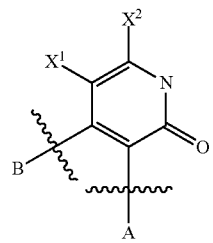
(T62) 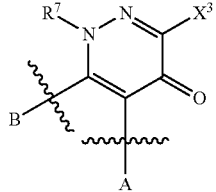
wherein in X, $X^1$, $X^2$, $X^3$, $X^4$, Y, $R^7$, A and B are as defined in claim 1.
6. The compound according to claim 1 wherein T is (Tp) or an optionally substituted pyrazolyl ring selected from the group consisting of:
(T1) 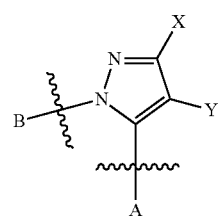
(T2) 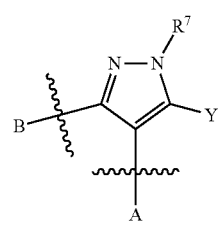

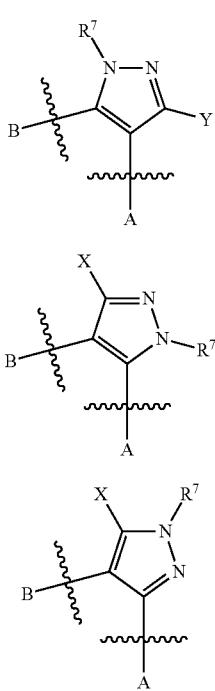

wherein,

X, Y, R⁷, A and B are as defined in claim 1.

7. The compound of claim 1, wherein T is selected from (T1), (T4), and (T5), and X is hydrogen or halogen.

8. The compound according to claim 6, wherein T is selected from (T4) and (T5) and X is halogen.

9. The compound according to claim 6, wherein T is selected from (T1), (T2), and (T3) and Y is hydrogen, $C_1$-$C_3$ alkyl, $C_1$-$C_3$haloalkyl, or halogen.

10. The compound according to claim 6, wherein T is selected from (T2), (T3), (T4), and (T5) wherein $R^7$ is $C_1$-$C_3$ alkyl, or $C_1$-$C_3$haloalkyl.

11. The compound according to claim 1, wherein T is (Tp) and $X^{21}$ is halogen, $C_1$-$C_3$alkyl, or $C_1$-$C_3$haloalkyl.

12. The compound according to claim 1 wherein T is (Tp) and $X^{24}$ is halogen, $C_1$-$C_3$alkyl, or $C_1$-$C_3$haloalkyl.

13. A herbicidal composition comprising a herbicidal compound according to claim 1 and an agriculturally acceptable formulation adjuvant.

14. A herbicidal composition according to claim 13, further comprising at least one additional pesticide.

15. A method of controlling unwanted plant growth, comprising applying a compound of formula (I) as defined in claim 1 to the unwanted plants or to the locus thereof.

* * * * *